US009988629B2

(12) United States Patent
Wakayama et al.

(10) Patent No.: US 9,988,629 B2
(45) Date of Patent: Jun. 5, 2018

(54) ANTISENSE NUCLEIC ACIDS

(71) Applicants: NIPPON SHINYAKU CO., LTD., Kyoto-shi, Kyoto (JP); NATIONAL CENTER OF NEUROLOGY AND PSYCHIATRY, Kodaira-shi, Tokyo (JP)

(72) Inventors: Tatsushi Wakayama, Ibaraki (JP); Haruna Seo, Tokyo (JP); Youhei Satou, Ibaraki (JP); Shin'ichi Takeda, Tokyo (JP); Tetsuya Nagata, Tokyo (JP)

(73) Assignees: NIPPON SHINYAKU CO., LTD., Kyoto-shi, Kyoto (JP); NATIONAL CENTER OF NEUROLOGY AND PSYCHIATRY, Kodaira-shi, Tokyo (JP)

( * ) Notice: Subject to any disclaimer, the term of this patent is extended or adjusted under 35 U.S.C. 154(b) by 0 days. days.

(21) Appl. No.: 15/122,435

(22) PCT Filed: Mar. 11, 2015

(86) PCT No.: PCT/JP2015/057180
§ 371 (c)(1),
(2) Date: Aug. 30, 2016

(87) PCT Pub. No.: WO2015/137409
PCT Pub. Date: Sep. 17, 2015

(65) Prior Publication Data
US 2017/0067048 A1 Mar. 9, 2017

(30) Foreign Application Priority Data
Mar. 12, 2014 (JP) .................... 2014-048897

(51) Int. Cl.
*C12N 15/113* (2010.01)
*A61K 31/713* (2006.01)
*C12N 15/11* (2006.01)

(52) U.S. Cl.
CPC .......... *C12N 15/113* (2013.01); *A61K 31/713* (2013.01); *C12N 15/111* (2013.01); *C12N 2310/11* (2013.01); *C12N 2310/314* (2013.01); *C12N 2310/3233* (2013.01); *C12N 2320/33* (2013.01)

(58) Field of Classification Search
None
See application file for complete search history.

(56) References Cited

U.S. PATENT DOCUMENTS

| 2003/0235845 A1 | 12/2003 | van Ommen et al. |
| 2007/0082861 A1 | 4/2007 | Matsuo et al. |
| 2008/0194463 A1* | 8/2008 | Weller .................. A61K 48/00 514/1.1 |
| 2010/0130591 A1 | 5/2010 | Sazani et al. |
| 2010/0168212 A1 | 7/2010 | Popplewell et al. |
| 2011/0263682 A1 | 10/2011 | De Kimpe et al. |
| 2011/0269665 A1 | 11/2011 | Kole |
| 2012/0065169 A1 | 3/2012 | Hanson et al. |
| 2012/0270925 A1* | 10/2012 | Wilton .................. C12N 15/111 514/44 A |
| 2013/0211062 A1 | 8/2013 | Watanabe et al. |

FOREIGN PATENT DOCUMENTS

| WO | WO-02/24906 A1 | 3/2002 |
| WO | WO-2004/048570 A1 | 6/2004 |
| WO | WO 2007/145661 * | 12/2007 |
| WO | WO-2010/048586 A1 | 4/2010 |
| WO | WO-2010/050801 A1 | 5/2010 |
| WO | WO-2011154427 A1 | 12/2011 |
| WO | WO-2012/029986 A1 | 3/2012 |
| WO | WO-2012/150960 A1 | 11/2012 |

OTHER PUBLICATIONS

Van Deutekom et al (Hum. Mol. Gen. 10(15):1547-1554, 2001).*
Kinali et al (Lancet Neurol 2009; 8: 918-28).*
Mann et al (J. Gene Med. 4(6):644-54, 2002).*
Wu et al (PLoS One 6(5): 12 pages, 2011).*
Aartsma-Rus et al (Mol. Ther. 17(3): 548-553, 2009).*
Annemieke Aartsma-Rus, et al., "Targeted exon skipping as a potential gene correction therapy for Duchenne muscular dystrophy," Neuromuscular Disorders 12 (2002) S71-S77.
Yoshitsugu Aoki, et al., "In-frame Dystrophin Following Exon 51-Skipping Improves Muscle Pathology and Function in the Exon 52-Deficient mdx Mouse," Molecular Therapy 2010, vol. 18, pp. 1995-2005.
V. Arechavala-Gomeza, et al., "Comparative Analysis of Antisense Oligonucleotide Sequences for Targeted Skipping of Exon 51 During Dystrophin Pre-mRNA Splicing in Human Muscle," Human Gene Therapy, 2007, vol. 18, No. 9, pp. 798-810.
Sebahattin Cirak, et al., "Exon skipping and dystrophin restoration in patients with Duchenne muscular dystrophy after systemic phosphorodiamidate morpholino oligomer treatment: an open-label, phase 2, dose-escalation study," Lancet, 2011, vol. 378, No. 9791, pp. 595-605.
Tania Incitti, et al., "Exon Skipping and Duchenne Muscular Dystrophy Therapy: Selection of the Most Active U1 snRNA-Antisense Able to Induce Dystrophin Exon 51 Skipping," Molecular Therapy, 2010, vol. 18, No. 9, pp. 1675-1682.
Masafumi Matsuo, "Duchenne/Becker muscular dystrophy: from molecular diagnosis to gene therapy," Brain & Development 1996; 18: pp. 167-172.
Anthony P. Monaco, et al., "An Explanation for the Phenotypic Differences between Patients Bearing Partial Deletions of the DMD Locus," Genomics 1998; 2: pp. 90-95.
Shiho Nakano, et al., "Exon-skipping events in candidates for clinical trials of morpholino," Pediatrics International 2011: 53: 524-529.

(Continued)

*Primary Examiner* — Richard A Schnizer
(74) *Attorney, Agent, or Firm* — Drinker Biddle & Reath LLP

(57) ABSTRACT

Provided is a drug that allows highly-efficient skipping of exon 51 in the human dystrophin gene. The present invention provides an antisense oligomer which enables exon 51 in the human dystrophin gene to be skipped.

10 Claims, 1 Drawing Sheet

(56) References Cited

OTHER PUBLICATIONS

Takashi Saito, et al., "Development of Exon Skipping Therapy for Duchenne Muscular Dystrophy Using Patients-Derived Cells," Japanese Journal of Clinical Pharmacology and Therapeutics, Mar. 2012, vol. 43, No. 2, pp. 91-92, including English translation.
Steve D. Wilton, et al., "Antisense Oligonucleotide-induced Exon Skipping Across the Human Dystrophin Gene Transcript," Molecular Therapy 2007: 15: pp. 1288-1296.
International Search Report dated Jun. 16, 2015 for PCT/JP2015/057180.
EP Application 15761392.8—Extended European Search Report dated Sep. 8, 2017.
De Angelis, et al., "Chimeric snRNA molecules carrying antisense sequences against the splice junctions of exon 51 of the dystrophin pre-mRNA induce exon skipping and restoration of a dystrophin synthesis in Δ48-50 DMD cells", Proceedings of the National Academy of Science USA, Jul. 9, 2002, vol. 99, No. 14, pp. 9456-9461.

\* cited by examiner

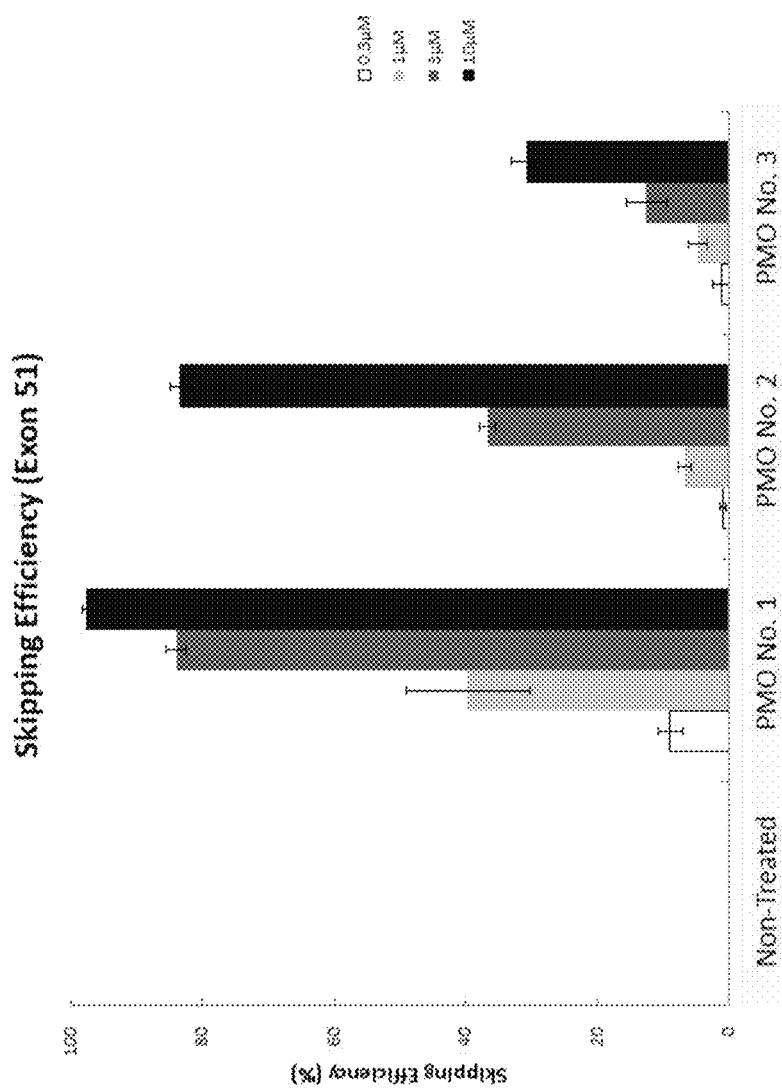

SEQUENCE LISTING

<160> NUMBER OF SEQ ID NOS: 34

<210> SEQ ID NO 1
<211> LENGTH: 30
<212> TYPE: DNA
<213> ORGANISM: Artificial Sequence
<220> FEATURE:
<223> OTHER INFORMATION: Synthetic Nucleic Acid

<400> SEQUENCE: 1
cggtaagttc tgtcctcaag gaagatggca                              30

<210> SEQ ID NO 2
<211> LENGTH: 30
<212> TYPE: DNA
<213> ORGANISM: Artificial Sequence
<220> FEATURE:
<223> OTHER INFORMATION: Synthetic Nucleic Acid

<400> SEQUENCE: 2
ctcatacctt ctgcttcaag gaagatggca                              30

<210> SEQ ID NO 3
<211> LENGTH: 233
<212> TYPE: DNA
<213> ORGANISM: Homo sapiens

<400> SEQUENCE: 3
ctcctactca gactgttact ctggtgacac aacctgtggt tactaaggaa actgccatct    60
ccaaactaga aatgccatct tccttgatgt tggaggtacc tgctctggca gatttcaacc   120
gggcttggac agaacttacc gactggcttt ctctgcttga tcaagttata aaatcacaga   180
gggtgatggt gggtgacctt gaggatatca acgagatgat catcaagcag aag          233

<210> SEQ ID NO 4
<211> LENGTH: 30
<212> TYPE: DNA
<213> ORGANISM: Artificial Sequence
<220> FEATURE:
<223> OTHER INFORMATION: Synthetic Nucleic Acid

<400> SEQUENCE: 4
ctccaacatc aaggaagatg gcatttctag                              30

<210> SEQ ID NO 5
<211> LENGTH: 20
<212> TYPE: DNA
<213> ORGANISM: Artificial Sequence
<220> FEATURE:
<223> OTHER INFORMATION: Synthetic Nucleic Acid

<400> SEQUENCE: 5
ctgagtggaa ggcggtaaac                                         20

<210> SEQ ID NO 6
<211> LENGTH: 20
<212> TYPE: DNA
<213> ORGANISM: Artificial Sequence
<220> FEATURE:
<223> OTHER INFORMATION: Synthetic Nucleic Acid

<400> SEQUENCE: 6
gaagtttcag ggccaagtca                                         20

-continued

<210> SEQ ID NO 7
<211> LENGTH: 21
<212> TYPE: DNA
<213> ORGANISM: Artificial Sequence
<220> FEATURE:
<223> OTHER INFORMATION: Synthetic Nucleic Acid

<400> SEQUENCE: 7
aacatcaagg aagatggcat t                                              21

<210> SEQ ID NO 8
<211> LENGTH: 21
<212> TYPE: DNA
<213> ORGANISM: Artificial Sequence
<220> FEATURE:
<223> OTHER INFORMATION: Synthetic Nucleic Acid

<400> SEQUENCE: 8
tccaacatca aggaagatgg c                                              21

<210> SEQ ID NO 9
<211> LENGTH: 21
<212> TYPE: DNA
<213> ORGANISM: Artificial Sequence
<220> FEATURE:
<223> OTHER INFORMATION: Synthetic Nucleic Acid

<400> SEQUENCE: 9
acctccaaca tcaaggaaga t                                              21

<210> SEQ ID NO 10
<211> LENGTH: 21
<212> TYPE: DNA
<213> ORGANISM: Artificial Sequence
<220> FEATURE:
<223> OTHER INFORMATION: Synthetic Nucleic Acid

<400> SEQUENCE: 10
gaguaacagu cugaguagga g                                              21

<210> SEQ ID NO 11
<211> LENGTH: 21
<212> TYPE: DNA
<213> ORGANISM: Artificial Sequence
<220> FEATURE:
<223> OTHER INFORMATION: Synthetic Nucleic Acid

<400> SEQUENCE: 11
ugugucacca gaguaacagu c                                              21

<210> SEQ ID NO 12
<211> LENGTH: 21
<212> TYPE: DNA
<213> ORGANISM: Artificial Sequence
<220> FEATURE:
<223> OTHER INFORMATION: Synthetic Nucleic Acid

<400> SEQUENCE: 12
aaccacaggu ugugucacca g                                              21

<210> SEQ ID NO 13
<211> LENGTH: 21
<212> TYPE: DNA
<213> ORGANISM: Artificial Sequence
<220> FEATURE:
<223> OTHER INFORMATION: Synthetic Nucleic Acid

```
<400> SEQUENCE: 13
uuuccuuagu aaccacaggu u                                              21

<210> SEQ ID NO 14
<211> LENGTH: 21
<212> TYPE: DNA
<213> ORGANISM: Artificial Sequence
<220> FEATURE:
<223> OTHER INFORMATION: Synthetic Nucleic Acid

<400> SEQUENCE: 14
gagauggcag uuuccuuagu a                                              21

<210> SEQ ID NO 15
<211> LENGTH: 21
<212> TYPE: DNA
<213> ORGANISM: Artificial Sequence
<220> FEATURE:
<223> OTHER INFORMATION: Synthetic Nucleic Acid

<400> SEQUENCE: 15
uucuaguuug gagauggcag u                                              21

<210> SEQ ID NO 16
<211> LENGTH: 21
<212> TYPE: DNA
<213> ORGANISM: Artificial Sequence
<220> FEATURE:
<223> OTHER INFORMATION: Synthetic Nucleic Acid

<400> SEQUENCE: 16
aagauggcau uucuaguuug g                                              21

<210> SEQ ID NO 17
<211> LENGTH: 21
<212> TYPE: DNA
<213> ORGANISM: Artificial Sequence
<220> FEATURE:
<223> OTHER INFORMATION: Synthetic Nucleic Acid

<400> SEQUENCE: 17
aacaucaagg aagauggcau u                                              21

<210> SEQ ID NO 18
<211> LENGTH: 21
<212> TYPE: DNA
<213> ORGANISM: Artificial Sequence
<220> FEATURE:
<223> OTHER INFORMATION: Synthetic Nucleic Acid

<400> SEQUENCE: 18
agguaccucc aacaucaagg a                                              21

<210> SEQ ID NO 19
<211> LENGTH: 21
<212> TYPE: DNA
<213> ORGANISM: Artificial Sequence
<220> FEATURE:
<223> OTHER INFORMATION: Synthetic Nucleic Acid

<400> SEQUENCE: 19
cugccagagc agguaccucc a                                              21
```

<210> SEQ ID NO 20
<211> LENGTH: 21
<212> TYPE: DNA
<213> ORGANISM: Artificial Sequence
<220> FEATURE:
<223> OTHER INFORMATION: Synthetic Nucleic Acid

<400> SEQUENCE: 20
cgguugaaau cugccagagc a                                              21

<210> SEQ ID NO 21
<211> LENGTH: 21
<212> TYPE: DNA
<213> ORGANISM: Artificial Sequence
<220> FEATURE:
<223> OTHER INFORMATION: Synthetic Nucleic Acid

<400> SEQUENCE: 21
uguccaagcc cgguugaaau c                                              21

<210> SEQ ID NO 22
<211> LENGTH: 21
<212> TYPE: DNA
<213> ORGANISM: Artificial Sequence
<220> FEATURE:
<223> OTHER INFORMATION: Synthetic Nucleic Acid

<400> SEQUENCE: 22
cgguaaguuc uguccaagcc c                                              21

<210> SEQ ID NO 23
<211> LENGTH: 21
<212> TYPE: DNA
<213> ORGANISM: Artificial Sequence
<220> FEATURE:
<223> OTHER INFORMATION: Synthetic Nucleic Acid

<400> SEQUENCE: 23
gaaagccagu cgguaaguuc u                                              21

<210> SEQ ID NO 24
<211> LENGTH: 21
<212> TYPE: DNA
<213> ORGANISM: Artificial Sequence
<220> FEATURE:
<223> OTHER INFORMATION: Synthetic Nucleic Acid

<400> SEQUENCE: 24
aucaagcaga gaaagccagu c                                              21

<210> SEQ ID NO 25
<211> LENGTH: 21
<212> TYPE: DNA
<213> ORGANISM: Artificial Sequence
<220> FEATURE:
<223> OTHER INFORMATION: Synthetic Nucleic Acid

<400> SEQUENCE: 25
uuauaacuug aucaagcaga g                                              21

<210> SEQ ID NO 26
<211> LENGTH: 21
<212> TYPE: DNA
<213> ORGANISM: Artificial Sequence
<220> FEATURE:
<223> OTHER INFORMATION: Synthetic Nucleic Acid

<400> SEQUENCE: 26
cucugugauu uuauaacuug a                                               21

<210> SEQ ID NO 27
<211> LENGTH: 21
<212> TYPE: DNA
<213> ORGANISM: Artificial Sequence
<220> FEATURE:
<223> OTHER INFORMATION: Synthetic Nucleic Acid

<400> SEQUENCE: 27
caccaucacc cucugugauu u                                               21

<210> SEQ ID NO 28
<211> LENGTH: 21
<212> TYPE: DNA
<213> ORGANISM: Artificial Sequence
<220> FEATURE:
<223> OTHER INFORMATION: Synthetic Nucleic Acid

<400> SEQUENCE: 28
caaggucacc caccaucacc c                                               21

<210> SEQ ID NO 29
<211> LENGTH: 21
<212> TYPE: DNA
<213> ORGANISM: Artificial Sequence
<220> FEATURE:
<223> OTHER INFORMATION: Synthetic Nucleic Acid

<400> SEQUENCE: 29
uugauauccu caaggucacc c                                               21

<210> SEQ ID NO 30
<211> LENGTH: 21
<212> TYPE: DNA
<213> ORGANISM: Artificial Sequence
<220> FEATURE:
<223> OTHER INFORMATION: Synthetic Nucleic Acid

<400> SEQUENCE: 30
gaucaucucg uugauauccu c                                               21

<210> SEQ ID NO 31
<211> LENGTH: 21
<212> TYPE: DNA
<213> ORGANISM: Artificial Sequence
<220> FEATURE:
<223> OTHER INFORMATION: Synthetic Nucleic Acid

<400> SEQUENCE: 31
ucugcuugau gaucaucucg u                                               21

<210> SEQ ID NO 32
<211> LENGTH: 21
<212> TYPE: DNA
<213> ORGANISM: Artificial Sequence
<220> FEATURE:
<223> OTHER INFORMATION: Synthetic Nucleic Acid

<400> SEQUENCE: 32
ggcauuucua guuuggagau g                                               21

```
<210> SEQ ID NO 33
<211> LENGTH: 21
<212> TYPE: DNA
<213> ORGANISM: Artificial Sequence
<220> FEATURE:
<223> OTHER INFORMATION: Synthetic Nucleic Acid

<400> SEQUENCE: 33
caaggaagau ggcauuucua g                                               21

<210> SEQ ID NO 34
<211> LENGTH: 21
<212> TYPE: DNA
<213> ORGANISM: Artificial Sequence
<220> FEATURE:
<223> OTHER INFORMATION: Synthetic Nucleic Acid

<400> SEQUENCE: 34
ccuccaacau caaggaagau g                                               21
```

ANTISENSE NUCLEIC ACIDS

CROSS REFERENCE TO RELATED APPLICATIONS:

This application is the National Stage of International Application No. PCT/JP2015/057180, filed Mar. 11, 2015, and claims benefit of Japanese Application No. 2014-048897 filed on Mar. 12, 2014.

REFERENCE TO A SEQUENCE LISTING

The instant application contains a sequence listing which has been submitted in ASCII format via EFS-Web and is hereby incorporated by reference in its entirety. Said ASCII copy, created on Mar. 11, 2015, is named G1311_Sequence_Listing.txt and is 7,076 bytes in size.

TECHNICAL FIELD

The present invention relates to an antisense oligomer which causes skipping of exon 51 in the human dystrophin gene, and a pharmaceutical composition comprising the oligomer.

BACKGROUND ART

Duchenne muscular dystrophy (DMD) is the most frequent form of hereditary progressive muscular dystrophy that affects one in about 3,500 newborn boys. Although the motor functions are rarely different from healthy humans in infancy and childhood, muscle weakness is observed in children from around 4 to 5 years old. Then, muscle weakness progresses to the loss of ambulation by about 12 years old and death due to cardiac or respiratory insufficiency in the twenties. DMD is such a severe disorder. At present, there is no effective therapy for DMD available, and it has been strongly desired to develop a novel therapeutic agent.

DMD is known to be caused by a mutation in the dystrophin gene. The dystrophin gene is located on X chromosome and is a huge gene consisting of 2.2 million DNA nucleotide pairs. DNA is transcribed into mRNA precursors, and introns are removed by splicing to synthesize mRNA of 11,058 bases, in which 79 exons are joined together. This mRNA is translated into 3,685 amino acids to produce the dystrophin protein. The dystrophin protein is associated with the maintenance of membrane stability in muscle cells and necessary to make muscle cells less fragile. The dystrophin gene from patients with DMD contains a mutation and hence, the dystrophin protein, which is functional in muscle cells, is rarely expressed. Therefore, the structure of muscle cells cannot be maintained in the body of the patients with DMD, leading to a large influx of calcium ions into muscle cells. Consequently, an inflammation-like response occurs to promote fibrosis so that muscle cells can be regenerated only with difficulty.

Becker muscular dystrophy (BMD) is also caused by a mutation in the dystrophin gene. The symptoms involve muscle weakness accompanied by atrophy of muscle but are typically mild and slow in the progress of muscle weakness, when compared to DMD. In many cases, its onset is in adulthood. Differences in clinical symptoms between DMD and BMD are considered to reside in whether the reading frame for amino acids on the translation of dystrophin mRNA into the dystrophin protein is disrupted by the mutation or not (Non-Patent Document 1). More specifically, in DMD, the presence of mutation shifts the amino acid reading frame so that the expression of functional dystrophin protein is abolished, whereas in BMD the dystrophin protein that functions, though imperfectly, is produced because the amino acid reading frame is preserved, while a part of the exons are deleted by the mutation.

Exon skipping is expected to serve as a method for treating DMD. This method involves modifying splicing to restore the amino acid reading frame of dystrophin mRNA and induce expression of the dystrophin protein having the function partially restored (Non-Patent Document 2). The amino acid sequence part, which is a target for exon skipping, will be lost. For this reason, the dystrophin protein expressed by this treatment becomes shorter than normal one but since the amino acid reading frame is maintained, the function to stabilize muscle cells is partially retained. Consequently, it is expected that exon skipping will lead DMD to the similar symptoms to that of BMD which is milder. The exon skipping approach has passed the animal tests using mice or dogs and now is currently assessed in clinical trials on human DMD patients.

The skipping of an exon can be induced by binding of antisense nucleic acids targeting either 5' or 3' splice site or both sites, or exon-internal sites. An exon will only be included in the mRNA when both splice sites thereof are recognized by the spliceosome complex. Thus, exon skipping can be induced by targeting the splice sites with antisense nucleic acids. Furthermore, the binding of an SR protein to an exonic splicing enhancer (ESE) is considered necessary for an exon to be recognized by the splicing mechanism. Accordingly, exon skipping can also be induced by targeting ESE.

Since a mutation of the dystrophin gene may vary depending on DMD patients, antisense nucleic acids need to be designed based on the site or type of respective genetic mutation. In the past, antisense nucleic acids that induce exon skipping for all 79 exons were produced by Steve Wilton, et al., University of Western Australia (Non-Patent Document 3), and the antisense nucleic acids which induce exon skipping for 39 exons were produced by Annemieke Aartsma-Rus, et al., Netherlands (Non-Patent Document 4).

It is considered that approximately 13% of all DMD patients may be treated by skipping the exon 51 (hereinafter referred to as "exon 51"). In recent years, a plurality of research organizations reported on the studies where exon 51 in the dystrophin gene was targeted for exon skipping (Patent Documents 1 to 6; Non-Patent Documents 5 to 6). However, a technique for skipping exon 51 with a high efficiency has not yet been established.

PRIOR ART DOCUMENT

Patent Document

Patent Document 1: International Publication WO 2004/048570
Patent Document 2: International Publication WO 2002/024906
Patent Document 3: International Publication WO 2010/048586
Patent Document 4: International Publication WO 2010/050801
Patent Document 5: US 2010/0168212
Non-Patent Document 1: Monaco A. P. et al., Genomics 1988; 2: p. 90-95
Non-Patent Document 2: Matsuo M., Brain Dev 1996; 18: p. 167-172

Non-Patent Document 3: Wilton S. D., et al., Molecular Therapy 2007: 15: p. 1288-96

Non-Patent Document 4: Annemieke Aartsma-Rus et al., (2002) Neuromuscular Disorders 12: S71-S77

Non-Patent Document 5: Aoki Y., et al., Molecular therapy 2010: 18: p. 1995-2005

Non-Patent Document 6: Nakano S., et al., Pediatr Int. 2011: 53: 524-429

DISCLOSURE OF THE INVENTION

Problems to be Solved by the Invention

Under the foregoing circumstances, antisense oligomers that induce exon 51 skipping in the dystrophin gene with a high efficiency and muscular dystrophy therapeutics comprising oligomers thereof have been desired.

Means for Solving the Problem

As a result of detailed studies of the technical contents of the above documents and the structure of the dystrophin gene, the present inventors have found that exon 51 skipping can be induced with a high efficiency by administering the antisense oligomer having the nucleotide sequences represented by SEQ ID NO:1 and 2. Based on this finding, the present inventors have accomplished the present invention.

That is, the present invention is as follows.

[1] An antisense oligomer which is selected from a group consisting of (a) to (d) below:
 (a) an antisense oligomer comprising a nucleotide sequence of SEQ ID NO: 1 or 2;
 (b) an antisense oligomer which consists of a nucleotide sequence having deletion, substitution, insertion and/or addition of 1 to 5 nucleotides in the nucleotide sequence of SEQ ID NO: 1 or 2, and has an activity to cause skipping of the 51st exon in the human dystrophin gene;
 (c) an antisense oligomer which has a nucleotide sequence having at least 80% identity with a nucleotide sequence of SEQ ID NO: 1 or 2 and has an activity to cause skipping of the 51st exon in the human dystrophin gene; and
 (d) an antisense oligomer that hybridizes under stringent conditions to an oligonucleotide consisting of a nucleotide sequence complementary to the nucleotide sequence of SEQ ID NO: 1 or 2 and has an activity to cause skipping of the 51st exon in the human dystrophin gene.

[2] An antisense oligomer which is selected from a group consisting of (e) to (h) below:
 (e) an antisense oligomer which consists of a nucleotide sequence of SEQ ID NO: 1 or 2;
 (f) an antisense oligomer which consists of a nucleotide sequence having deletion, substitution, insertion and/or addition of 1 to 3 nucleotides in the nucleotide sequence of SEQ ID NO: 1 or 2, and has an activity to cause skipping of the 51st exon in the human dystrophin gene;
 (g) an antisense oligomer which consists of a nucleotide sequence having at least 80% identity with a nucleotide sequence of SEQ ID NO: 1 or 2 and has an activity to cause skipping of the 51st exon in the human dystrophin gene; and
 (h) an antisense oligomer that hybridizes under high stringent conditions to an oligonucleotide consisting of a nucleotide sequence complementary to a nucleotide sequence of SEQ ID NO: 1 or 2 and has an activity to cause skipping of the 51st exon in the human dystrophin gene.

[3] An antisense oligomer which is selected from a group consisting of (i) and (j) below:
 (i) an antisense oligomer which consists of a nucleotide sequence of SEQ ID NO: 1 or 2; and
 (j) an antisense oligomer which has a nucleotide sequence having at least 90% identity with a nucleotide sequence of SEQ ID NO: 1 or 2 and has an activity to cause skipping of the 51st exon in the human dystrophin gene.

[4] The antisense oligomer according to any one of [1] to [3] above, which is an oligonucleotide.

[5] The antisense oligomer according to [4] above, wherein the sugar moiety and/or the phosphate-binding region of at least one nucleotide constituting the oligonucleotide is modified.

[6] The antisense oligomer according to [4] or [5] above, wherein the sugar moiety of at least one nucleotide constituting the oligonucleotide is a ribose in which the 2'—OH group is replaced by any one selected from the group consisting of OR, R, R'OR, SH, SR, $NH_2$, NHR, $NR_2$, $N_3$, CN, F, Cl, Br and I (wherein R is an alkyl or an aryl and R' is an alkylene).

[7] The antisense oligomer according to any one of [4] to [6] above, wherein the phosphate-binding region of at least one nucleotide constituting the oligonucleotide is any one selected from the group consisting of a phosphorothioate bond, a phosphorodithioate bond, an alkylphosphonate bond, a phosphoramidate bond and a boranophosphate bond.

[8] The antisense oligomer according to any one of [1] to [3] above, which is a morpholino oligomer.

[9] The antisense oligomer according to [8] above, wherein the morpholine ring moiety, the phosphate-binding region, 3'-end and/or 5'-end of at least one morpholino constituting the morpholino oligomer is modified.

[10] The antisense oligomer according to [9] or [10] above, wherein the phosphate-binding region of at least one morpholino constituting the morpholino oligomer is any one selected from a phosphorodiamidate bond, a phosphorothioate bond, a phosphorodithioate bond, an alkylphosphonate bond, a phosphoramidate bond and a boranophosphate bond.

[11] The antisense oligomer according to [10] above, which is a phosphorodiamidate morpholino oligomer.

[12] The antisense oligomer according to any one of [9] to [11] above, wherein the 5' end is any one of chemical formulae (1) to (3) below:

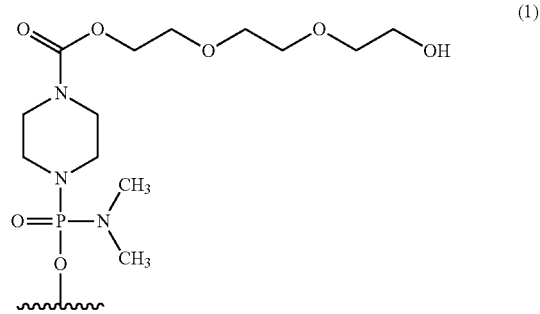

(1)

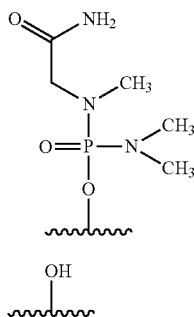

(2)

(3)

[13] A pharmaceutical composition for the treatment of muscular dystrophy, comprising as an active ingredient the antisense oligomer according to any one of [1] to [12] above, or a pharmaceutically acceptable salt or hydrate thereof.

[14] The pharmaceutical composition according to [13] above, comprising a pharmaceutically acceptable carrier.

[15] A method for treatment of muscular dystrophy, which comprises administering to a patient with muscular gystrophy the antisense oligomer according to any one of [1] to [12] above or the pharmaceutical composition according to [13] or [14] above.

[16] The method for treatment according to [15] above, wherein the patient with muscular dystrophy is a patient with deletions of nucleotides within exons 29-50, 50, 45-50, 48-50, 49-50, 52, 52-63, 13-50, 19-50, 43-50 or 47-50.

[17] The method for treatment according to [15] or [16] above, wherein the patient is a human.

[18] The use of the antisense oligomer according to any one of [1] to [12] above in manufacturing of the pharmaceutical composition for the treatment of muscular gystrophy.

[19] The antisense oligomer according to any one of [1] to [12] above, for use in the treatment of muscular dystrophy.

[20] The antisense oligomer according to [19] above, wherein the patient with muscular dystrophy in the said treatment is a patient with deletions of nucleotides within exons 29-50, 50, 45-50, 48-50, 49-50, 52, 52-63, 13-50, 19-50, 43-50 or 47-50.

[21] The antisense oligomer according to [19] or [20] above, wherein the patient is a human.

Effects of the Invention

The antisense oligomer of the present invention can induce skipping of exon 51 in the human dystrophin gene with a high efficiency. Also, the symptoms of Duchenne muscular dystrophy can be effectively alleviated by administering the pharmaceutical composition of the present invention.

BRIEF DESCRIPTION OF THE DRAWINGS

FIG. 1 shows the efficiency of exon 51 skipping in the human dystrophin gene in human rhabdomyosarcoma cell line (RD cells).

MODE FOR CARRYING OUT THE INVENTION

Hereinafter, the present invention is described in detail. The embodiments described below are intended to be presented by way of example merely to describe the invention but not limited only to the following embodiments. The present invention may be implemented in various ways without departing from the gist of the invention.

1. Antisense Oligomer

The present invention provides the antisense oligomer (hereinafter referred to as the "antisense oligomer of the present invention") which causes skipping of exon 51 in the human dystrophin gene with a high efficiency.

[Exon 51 in Human Dystrophin Gene]

In the present invention, the term "gene" is intended to mean a genomic gene and also include cDNA, mRNA precursor and mRNA. Preferably, the gene is mRNA precursor, i.e. pre-mRNA.

In the human genome, the human dystrophin gene locates at locus Xp21.2. The human dystrophin gene has a size of 2.2 million nucleotide pairs and is the largest gene among known human genes. However, the coding regions of the human dystrophin gene are only 14 kb, distributed as 79 exons throughout the human dystrophin gene (Roberts, R G, et al., Genomics, 16: 536-538 (1993)). The pre-mRNA, which is the transcript of the human dystrophin gene, undergoes splicing to generate mature mRNA of 14 kb. The nucleotide sequence of human wild-type dystrophin gene is known (GeneBank Accession No. NM_004006).

The nucleotide sequence of exon 51 in the human wild-type dystrophin gene is represented by SEQ ID NO: 3.

[Antisense Oligomer]

The antisense oligomer of the present invention is designed to cause skipping of exon 51 in the human dystrophin gene, thereby modifying the protein encoded by DMD type of dystrophin gene into the BMD type of dystrophin protein. Accordingly, exon 51 in the dystrophin gene that is the target of exon skipping by the antisense oligomer includes both wild and mutant types.

The antisense oligomer of the present invention is specifically the antisense oligomer which is selected from a group consisting of (a) to (d) below.

(a) an antisense oligomer comprising a nucleotide sequence of SEQ ID NO: 1 or 2;

(b) an antisense oligomer which consists of a nucleotide sequence having deletion, substitution, insertion and/or addition of 1 to 5 nucleotides in the nucleotide sequence of SEQ ID NO: 1 or 2, and has an activity to cause skipping of the 51st exon in the human dystrophin gene;

(c) an antisense oligomer which has a nucleotide sequence having at least 80% identity with a nucleotide sequence of SEQ ID NO: 1 or 2 and has an activity to cause skipping of exon 51 in the human dystrophin gene; and (d) an antisense oligomer that hybridizes under stringent conditions to an oligonucleotide consisting of a nucleotide sequence complementary to the nucleotide sequence of SEQ ID NO: 1 or 2 and has an activity to cause skipping of exon 51 in the human dystrophin gene.

The antisense oligomers of (b) to (d) are mutants of the antisense oligomer of (a) in particular and are intended to correspond to mutations of the dystrophin gene of the patients, e.g. polymorphism.

As another embodiment, the antisense oligomer of the present invention is specifically the antisense oligomer which is selected from a group consisting of (k) to (n) below.

(k) An antisense oligomer comprising the nucleotide sequence shown by any one of the SEQ ID NOS: 6 to 33;

(l) An antisense oligomer which consists of a nucleotide sequence having deletion, substitution, insertion and/or addition of 1 to 5 nucleotides in the nucleotide sequence shown by any one of the SEQ ID NOS: 6 to 33, and has an activity to cause skipping of exon 51 in the human dystrophin gene;

(m) An antisense oligomer which has a nucleotide sequence having at least 80% identity with a nucleotide sequence of any one of the SEQ ID NOS: 6 to 33 and has an activity to cause skipping of exon 51 in the human dystrophin gene; and (n) An antisense oligomer that hybridizes under stringent conditions to an oligonucleotide consisting of a nucleotide sequence complementary to the nucleotide sequence shown by any one of the SEQ ID NOS: 6 to 33 and has an activity to cause skipping of exon 51 in the human dystrophin gene.

The antisense oligomers of (l) to (n) are mutants of the antisense oligomer of (k) in particular and are intended to correspond to mutations, of the dystrophin gene of the patients, e.g. polymorphism.

Also, the antisense oligomer of the present invention is the antisense oligomer which is selected from a group consisting of (o) to (r) below.

(o) An antisense oligomer which consists of the nucleotide sequence shown by any one of the SEQ ID NOS: 6 to 33;

(p) An antisense oligomer which consists of a nucleotide sequence having deletion, substitution, insertion and/or addition of 1 to 3 nucleotides in the nucleotide sequence shown by any one of the SEQ ID NOS: 6 to 33, and has an activity to cause skipping of exon 51 in the human dystrophin gene;

(q) An antisense oligomer which has a nucleotide sequence having at least 80% identity with a nucleotide sequence of any one of the SEQ ID NOS: 6 to 33 and has an activity to cause skipping of exon 51 in the human dystrophin gene; and (r) An antisense oligomer that hybridizes under high stringent conditions to an oligonucleotide consisting of a nucleotide sequence complementary to the nucleotide sequence shown by any one of the SEQ ID NOS: 6 to 33 and has an activity to cause skipping of exon 51 in the human dystrophin gene.

Furthermore, the antisense oligomer of the present invention is the antisense oligomer which is selected from a group consisting of (i) and (j) below:

(i) an antisense oligomer consisting of a nucleotide sequence of any one of the SEQ ID NOS: 6 to 33; or (j) an antisense oligomer which consists of a nucleotide sequence having at least 90% identity with a nucleotide sequence of any one of the SEQ ID NOS: 6 to 33 and has an activity to cause skipping of exon 51 in the human dystrophin gene.

As used herein, the term "antisense oligomer that hybridizes under stringent conditions" refers to, for example, an antisense oligomer obtained by colony hybridization, plaque hybridization, Southern hybridization or the like, using as a probe all or part of an oligonucleotide consisting of a nucleotide sequence complementary to the nucleotide sequence of, e.g., SEQ ID NO: 1. The hybridization method which may be used includes methods described in, for example, "Sambrook & Russell, Molecular Cloning: A Laboratory Manual Vol. 3, Cold Spring Harbor, Laboratory Press 2001," "Ausubel, Current Protocols in Molecular Biology, John Wiley & Sons 1987-1997," etc.

As used herein, the term "stringent conditions" may be any of low stringent conditions, moderate stringent conditions or high stringent conditions. The term "low stringent condition" is, for example, 5×SSC, 5×Denhardt's solution, 0.5% SDS, 50% formamide at 32° C. The term "moderate stringent condition" is, for example, 5×SSC, 5×Denhardt's solution, 0.5% SDS, 50% formamide at 42° C., or 5×SSC, 1% SDS, 50 mM Tris-HCl (pH 7.5), 50% formamide at 42° C. The term "high stringent condition" is, for example, (1) 5×SSC, 5×Denhardt's solution, 0.5% SDS, 50% formamide at 50° C., (2) 0.2×SSC, 0.1% SDS at 60° C., (3) 0.2×SSC, 0.1% SDS at 62° C., (4) 0.2×SSC, 0.1% SDS at 65° C., or (5) 0.1×SSC, 0.1% SDS at 65° C., but is not limited thereto. Under these conditions, antisense oligomer with higher homology are expected to be obtained efficiently at higher temperatures, although multiple factors are involved in hybridization stringency including temperature, probe concentration, probe length, ionic strength, time, salt concentration and others, and those skilled in the art may approximately select these factors to achieve similar stringency.

When commercially available kits are used for hybridization, for example, an Alkphos Direct Labelling and Detection System (GE Healthcare) may be used. In this case, according to the attached protocol, after cultivation with a labeled probe overnight, the membrane is washed with a primary wash buffer containing 0.1% (w/v) SDS at 55° C., thereby detecting hybridized antisense oligomer. Alternatively, when the probe is labeled with digoxigenin (DIG) using a commercially available reagent (e.g., a POR Labelling Mix (Roche Diagnostics), etc.) in producing a probe based on all or part of the complementary sequence to the nucleotide sequence of SEQ ID NO: 3, hybridization can be detected with a DIG Nucleic Acid Detection Kit (Roche Diagnostics).

In addition to the antisense oligomer described above, other antisense oligomer that can be hybridized include antisense oligomers having 90% or higher, 91% or higher, 92% or higher, 93% or higher, 94% or higher, 95% or higher, 96% or higher, 97% or higher, 98% or higher, 99% or higher, 99.1% or higher, 99.2% or higher, 99.3% or higher, 99.4% or higher, 99.5% or higher, 99.6% or higher, 99.7% or higher, 99.8% or higher, and 99.9% or higher identity with the nucleotide sequence of SEQ ID NO: 1 or 2, as calculated by homology search software such as FASTA and BLAST using the default parameters.

The identity between nucleotide sequences may be determined using FASTA (Science 227 (4693): 1435-1441, (1985)) or algorithm BLAST (Basic Local Alignment Search Tool) by Karlin and Altschul (Proc. Natl. Acad. Sci. USA 872264-2268, 1990; Proc. Natl. Acad. Sci. USA 90: 5873, 1993). Programs called blastn, blastx, tblastn and tblastx based on the BLAST algorithm have been developed (Altschul S F, et al: J. Mol. Biol. 215: 403, 1990). When a nucleotide sequence is sequenced using blastn, the parameters are, for example, score=100 and wordlength=12. When BLAST and Gapped BLAST programs are used, the default parameters for each program are employed.

The term "cause skipping of the exon 51 in the human dystrophin gene" is intended to mean that by binding of the antisense oligomer of the present invention to the site corresponding to exon 51 of the transcript (e.g., pre-mRNA) of the human dystrophin gene, for example, the nucleotide sequence corresponding to the 5' end of exon 53 is spliced at the nucleotide sequence corresponding to the 3' end of exon 50 in DMD patients with deletion of exon 52 when the transcript undergoes splicing, thus resulting in formation of mature mRNA which is free of codon frame shift.

Herein, the term "binding" described above is intended to mean that when the antisense oligomer of the present invention is mixed with the transcript of human dystrophin gene, both are hybridized under physiological conditions to form a double strand nucleic acid. The term "under physiological conditions" refers to conditions set to mimic the in vivo environment in terms of pH, salt composition and temperature. The conditions are, for example, 25 to 40° C., preferably 37° C., pH 5 to 8, preferably pH 7.4 and 150 mM of sodium chloride concentration.

Whether the skipping of exon 51 in the human dystrophin gene is caused or not can be confirmed by introducing the antisense oligomer of the present invention into a dystrophin expression cell (e.g., human rhabdomyosarcoma cells), amplifying the region surrounding exon 51 of mRNA of the human dystrophin gene from the total RNA of the dystrophin expression cell by RT-PCR and performing nested PCR or sequence analysis on the PCR amplified product.

The skipping efficiency can be determined as follows. The mRNA for the human dystrophin gene is collected from test cells; in the mRNA, the polynucleotide level "A" of the band where exon 51 is skipped and the polynucleotide level "B" of the band where exon 51 is not skipped are measured. Using these measurement values of "A" and "B," the efficiency is calculated by the following equation:

Skipping efficiency (%)=$A/(A+B) \times 100$

Preferably, the antisense oligomer of the present invention cause skipping of exon 51 with the efficiency of 10% or higher, 20% or higher, 30% or higher, 40% or higher, 50% or higher, 60% or higher, 70% or higher, 80% or higher, and 90% or higher. For calculation of the efficiency of skipping, International Publication WO2012/029986 may be referred.

The antisense oligomer of the present invention includes, for example, an oligonucleotide, morpholino oligomer or peptide nucleic acid (PNA), having a length of 16 to 35 nucleotides. The length is preferably from 19 to 32, from 20 to 31, 21 or 30 nucleotides and morpholino oligomers are preferred.

The oligonucleotide described above (hereinafter referred to as "the oligonucleotide of the present invention") is the antisense oligomer of the present invention composed of nucleotides as constituent units. Such nucleotides may be any of ribonucleotides, deoxyribonucleotides and modified nucleotides.

The modified nucleotide refers to one having fully or partly modified nucleobases, sugar moieties and/or phosphate-binding regions, which constitute the ribonucleotide or deoxyribonucleotide.

In the present invention, the nucleobase includes, for example, adenine, guanine, hypoxanthine, cytosine, thymine, uracil, and modified bases thereof. Examples of such modified bases include, but not limited to, pseudouracil, 3-methyluracil, dihydrouracil, 5-alkylcytosines (e.g., 5-methylcytosine), 5-alkyluracils (e.g., 5-ethyluracil), 5-halouracils (5-bromouracil), 6-azapyrimidine, 6-alkylpyrimidines (6-methyluracil), 2-thiouracil, 4-thiouracil, 4-acetylcytosine, 5-(carboxyhydroxymethyl) uracil, 5'-carboxymethylaminomethyl-2-thiouracil, 5-carboxymethylaminomethyluracil, 1-methyladenine, 1-methylhypoxanthine, 2,2-dimethylguanine, 3-methylcytosine, 2-methyladenine, 2-methylguanine, N6-methyladenine, 7-methylguanine, 5-methoxyaminomethyl-2-thiouracil, 5-methylaminomethyluracil, 5-methylcarbonylmethyluracil, 5-methyloxyuracil, 5-methyl-2-thiouracil, 2-methylthio-N6-isopentenyladenine, uracil-5-oxyacetic acid, 2-thiocytosine, purine, 2,6-diaminopurine, 2-aminopurine, isoguanine, indole, imidazole, xanthine, etc.

Modification of the sugar moiety may include, for example, modifications at the 2'-position of ribose and modifications of the other positions of the sugar. The modification at the 2'-position of ribose includes replacement of the 2'-OH of ribose with OR, R, R'OR, SH, SR, $NH_2$, NHR, $NR_2$, $N_3$, CN, F, Cl, Br or I, wherein R represents an alkyl or an aryl and R' represents an alkylene.

The modification for the other positions of the sugar includes, for example, replacement of O at the 4' position of ribose or deoxyribose with S, bridging between 2' and 4' positions of the sugar, e.g., LNA (locked nucleic acid) or ENA (2'-O,4'-C-ethylene-bridged nucleic acids), but is not limited thereto.

A modification of the phosphate-binding region includes, for example, a modification of replacing phosphodiester bond with phosphorothioate bond, phosphorodithioate bond, alkyl phosphonate bond, phosphoroamidate bond or boranophosphate bond (Enya et al: Bioorganic & Medicinal Chemistry, 2008, 18, 9154-9160) (cf., e.g., Japan Domestic Re-Publications of PCT Application Nos. 2006/129594 and 20061038608).

In this invention, the alkyl is preferably a straight or branched alkyl having 1 to 6 carbon atoms. Specific examples include methyl, ethyl, n-propyl, isopropyl, n-butyl, isobutyl, sec-butyl, tert-butyl, n-pentyl, isopentyl, neopentyl, tert-pentyl, n-hexyl and isohexyl. The alkyl may optionally be substituted. Examples of such substituents are a halogen, an alkoxy, cyano and nitro. The alkyl may be substituted with 1 to 3 substituents.

In this invention, the cycloalkyl is preferably a cycloalkyl having 5 to 12 carbon atoms. Specific examples include cyclopentyl, cyclohexyl, cycloheptyl, cyclooctyl, cyclodecyl and cyclododecyl.

In this invention, the halogen includes fluorine, chlorine, bromine and iodine.

The alkoxy is a straight or branched alkoxy having 1 to 6 carbon atoms such as methoxy, ethoxy, n-propoxy, isopropoxy, n-butoxy, isobutoxy, sec-butoxy, tert-butoxy, n-pentyloxy, isopentyloxy, n-hexyloxy, isohexyloxy, etc. Among others, an alkoxy having 1 to 3 carbon atoms is preferred.

In this invention, the aryl is preferably an aryl having 6 to 10 carbon atoms. Specific examples include phenyl, α-naphthyl and β-naphthyl. Among others, phenyl is preferred. The aryl may optionally be substituted. Examples of such substituents are an alkyl, a halogen, an alkoxy, cyano and nitro. The aryl may be substituted with one to three of such substituents.

In this invention, the alkylene is preferably a straight or branched alkylene having 1 to 6 carbon atoms. Specific examples include methylene, ethylene, trimethylene, tetramethylene, pentamethylene, hexamethylene, 2-(ethyl) trimethylene and 1-(methyl) tetramethylene.

In this invention, the acyl includes a straight or branched alkanoyl or aroyl. Examples of the alkanoyl include formyl, acetyl, 2-methylacetyl, 2,2-dimethylacetyl, propionyl, butyryl, isobutyryl, pentanoyl, 2,2-dimethylpropionyl, hexanoyl, etc. Examples of the aroyl include benzoyl, toluoyl and naphthoyl. The aroyl may optionally be substituted at substitutable positions and may be substituted with an alkyl(s).

Preferably, the oligonucleotide of the present invention is the antisense oligomer of the present invention containing a constituent unit represented by general formula below wherein the —OH group at position 2' of ribose is substituted with methoxy and the phosphate-binding region is a phosphorothioate bond:

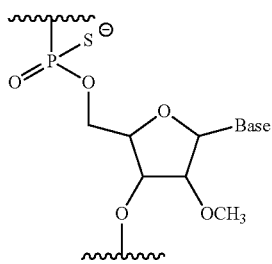

wherein Base represents a nucleobase.

The oligonucleotide of the present invention may be easily synthesized using various automated synthesizer (e.g., AKTA oligopilot plus 10/100 (GE Healthcare)). Alternatively, the synthesis may also be entrusted to a third-party organization (e.g., Promega Inc., Takara Co., or Japan Bio Service Co.), etc.

The morpholino oligomer of the present invention is the antisense oligomer of the present invention comprising the constituent unit represented by general formula below:

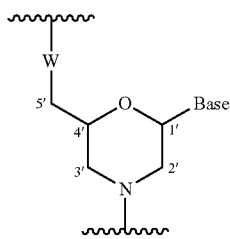

wherein Base has the same significance as defined above, and,

W represents a group shown by any one of the following groups:

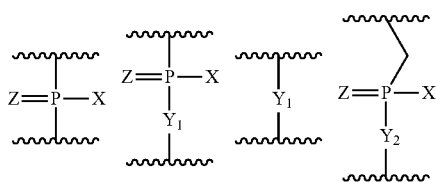

wherein X represents —CH$_2$R$^1$, —O—CH$_2$R$^1$, —S—CH$_2$R$^1$, —NR$^2$R$^3$ or F;

R$^1$ represents H or an alkyl;

R$^2$ and R$^3$, which may be the same or different, each represents H, an alkyl, a cycloalkyl or an aryl;

Y$_1$ represents O, S, CH$_2$ or NR$^1$;

Y$_2$ represents O, S or NR$^1$;

Z represents O or S.

Preferably, the morpholino oligomer is an oligomer comprising a constituent unit represented by general formula below (phosphorodiamidate morpholino oligomer (hereinafter referred to as "PMO")).

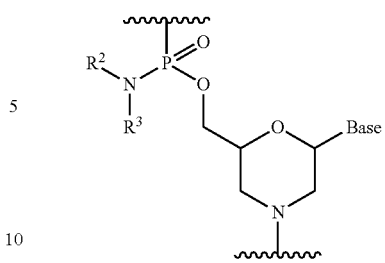

wherein Base, R$^2$ and R$^3$ have the same significance as defined above.

The morpholino oligomer of the present invention comprises one having fully or partly modified nucleobases, morpholine ring moieties, phosphate-binding regions, 3'-end and/or 5'-end which constitute the morpholino oligomer.

A modification of the phosphate-binding region includes, for example, a modification of replacing with phosphorodiamidate bond, phosphorothioate bond, phosphorodithioate bond, alkylphosphonate bond, phosphoramidate bond and boranophosphate bond (Enya et al: Bioorganic & Medicinal Chemistry, 2008, 18, 9154-9160) (cf., e.g., Japan Domestic Re-Publications of PCT Application Nos. 2006/129594 and 2006/038608).

The morpholino oligomer may be produced in accordance with, e.g., WO 1991/009033 or WO 2009/064471. In particular, PMO can be produced by the procedure described in WO 2009/064471 or produced by the process shown below.

[Method for Producing PMO]

An embodiment of PMO is, for example, the compound represented by general formula (I) below (hereinafter PMO (I)).

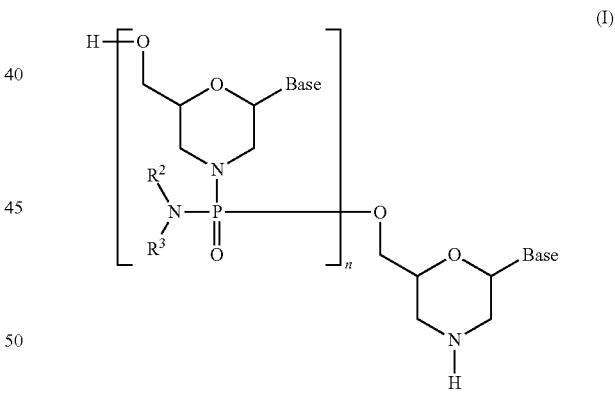

(I)

wherein Base, R$^2$ and R$^3$ have the same significance as defined above; and, n is a given integer of 1 to 99, preferably a given integer of 24 to 34, 27 to 31 or 28 to 30, preferably 29.

PMO (I) can be produced in accordance with a known method, for example, can be produced by performing the procedures in the following steps.

The compounds and reagents used in the steps below are not particularly limited so long as they are commonly used to prepare PMO.

Also, the following steps can all be carried out by the liquid phase method or the solid phase method (using manuals or commercially available solid phase automated synthesizers). In producing PMO by the solid phase method, it is desired to use automated synthesizers in view of simple operation procedures and accurate synthesis.

(1) Step A:

The compound represented by general formula (II) below (hereinafter referred to as Compound (II)) is reacted with an acid to prepare the compound represented by general formula (III) below (hereinafter referred to as Compound (III)):

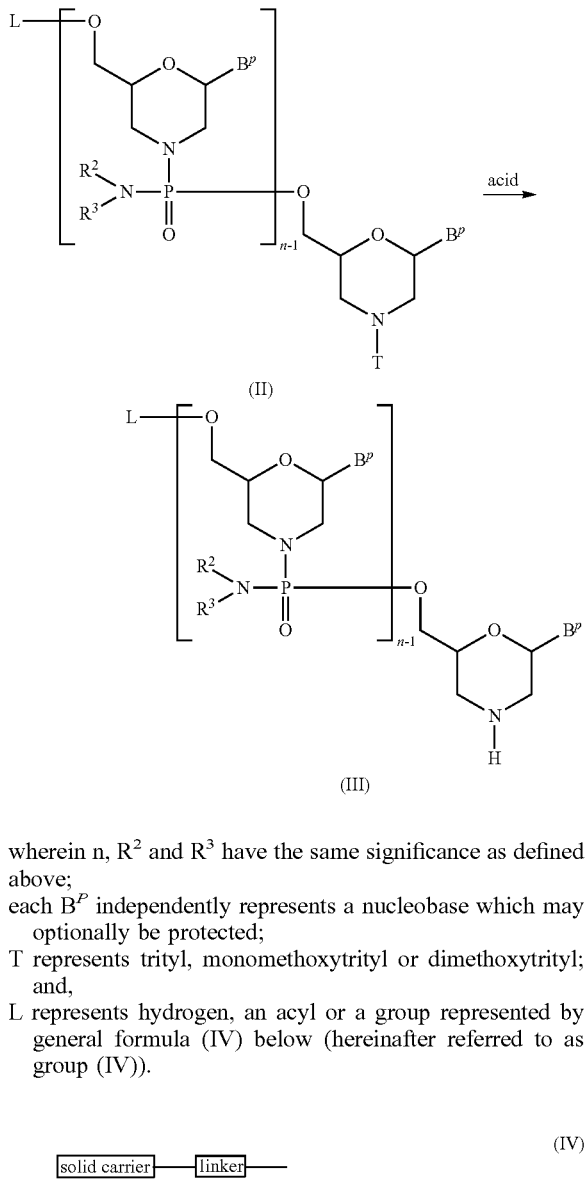

wherein n, $R^2$ and $R^3$ have the same significance as defined above;

each $B^P$ independently represents a nucleobase which may optionally be protected;

T represents trityl, monomethoxytrityl or dimethoxytrityl; and,

L represents hydrogen, an acyl or a group represented by general formula (IV) below (hereinafter referred to as group (IV)).

|solid carrier|—|linker|—         (IV)

The "nucleobase" for $B^P$ includes the same "nucleobase" as in Base, provided that the amino or hydroxy group in the nucleobase shown by $B^P$ may be protected. Such protective group for amino is not particularly limited so long as it is used as a protective group for nucleic acids. Specific examples include benzoyl, 4-methoxybenzoyl, acetyl, propionyl, butyryl, isobutyryl, phenylacetyl, phenoxyacetyl, 4-tert-butylphenoxyacetyl, 4-isopropylphenoxyacetyl and (dimethylamino)methylene. Specific examples of the protective group for the hydroxy group include 2-cyanoethyl, 4-nitrophenethyl, phenylsulfonylethyl, methylsulfonylethyl and trimethylsilylethyl, and phenyl, which may be substituted by 1 to 5 electron-withdrawing group at optional substitutable positions, diphenylcarbamoyl, dimethylcarbamoyl, diethylcarbamoyl, methylphenylcarbamoyl, 1-pyrolidinylcarbamoyl, morpholinocarbamoyl, 4-(tert-butylcarboxy) benzyl, 4-[(dimethylamino)carboxy]benzyl and 4-(phenylcarboxy)benzyl, (cf., e.g., WO 2009/064471).

The "solid carrier" is not particularly limited so long as it is a carrier usable for the solid phase reaction of nucleic acids. It is desired for the solid carrier to have the following properties: e.g., (i) it is sparingly soluble in reagents that can be used for the synthesis of morpholino nucleic acid derivatives (e.g., dichloromethane, acetonitrile, tetrazole, N-methylimidazole, pyridine, acetic anhydride, lutidine, trifluoroacetic acid); (ii) it is chemically stable to the reagents usable for the synthesis of morpholino nucleic acid derivatives; (iii) it can be chemically modified; (iv) it can be charged with desired morpholino nucleic acid derivatives; (v) it has a strength sufficient to withstand high pressure through treatments; and (vi) it has a uniform particle diameter range and distribution. Specifically, swellable polystyrene (e.g., aminomethyl polystyrene resin 1% divinylbenzene crosslinked (200-400 mesh) (2.4-3.0 mmol/g) (manufactured by Tokyo Chemical Industry), Aminomethylated Polystyrene Resin HCl [divinylbenzene 1%, 100-200 mesh] (manufactured by Peptide Institute, Inc.)), non-swellable polystyrene (e.g., Primer Support (manufactured by GE Healthcare)), PEG chain-attached polystyrene (e.g., $NH_2$-PEG resin (manufactured by Watanabe Chemical Co.), TentaGel resin), controlled pore glass (controlled pore glass; CPG) (manufactured by, e.g., CPG), oxalyl-controlled pore glass (cf., e.g., Alul et al., Nucleic Acids Research, Vol. 19, 1527 (1991)), TentaGel support-aminopolyethylene glycol-derivatized support (e.g., Wright et al., cf., Tetrahedron Letters, Vol. 34, 3373 (1993)), and a copolymer of Poros-polystyrene/divinylbenzene.

A "linker" which can be used is a known linker generally used to connect nucleic acids or morpholino nucleic acid derivatives. Examples include 3-aminopropyl, succinyl, 2,2'-diethanolsulfonyl and a long chain alkyl amino (LCAA).

This step can be performed by reacting Compound (II) with an acid.

The "acid" which can be used in this step includes, for example, trifluoroacetic acid, dichloroacetic acid and trichloroacetic acid. The acid used is appropriately in a range of, for example, 0.1 mol equivalent to 1000 mol equivalents based on 1 mol of Compound (II), preferably in a range of 1 mol equivalent to 100 mol equivalents based on 1 mol of Compound (II).

An organic amine can be used in combination with the acid described above. The organic amine is not particularly limited and includes, for example, triethylamine. The amount of the organic amine used is appropriately in a range of, e.g., 0.01 mol equivalent to 10 mol equivalents, and preferably in a range of 0.1 mol equivalent to 2 mol equivalents, based on 1 mol of the acid.

When a salt or mixture of the acid and the organic amine is used in this step, the salt or mixture includes, for example, a salt or mixture of trifluoroacetic acid and triethylamine, and more specifically, a mixture of 1 equivalent of triethylamine and 2 equivalents of trifluoroacetic acid.

The acid which can be used in this step may also be used in the form of a dilution with an appropriate solvent in a concentration of 0.1% to 30%. The solvent is not particularly limited as far as it is inert to the reaction, and includes, for example, dichloromethane, acetonitrile, an alcohol (ethanol, isopropanol, trifluoroethanol, etc.), water, or a mixture thereof.

The reaction temperature in the reaction described above is preferably in a range of, e.g., 10° C. to 50° C., more preferably, in a range of 20° C. to 40° C., and most preferably, in a range of 25° C. to 35° C.

The reaction time may vary depending upon kind of the acid used and reaction temperature, and is appropriately in a range of 0.1 minute to 24 hours in general, and preferably in a range of 1 minute to 5 hours.

After completion of this step, a base may be added, if necessary, to neutralize the acid remained in the system. The "base" is not particularly limited and includes, for example, diisopropylamine. The base may also be used in the form of a dilution with an appropriate solvent in a concentration of 0.1% (v/v) to 30% (v/v).

The solvent used in this step is not particularly limited so long as it is inert to the reaction, and includes dichloromethane, acetonitrile, an alcohol (ethanol, isopropanol, trifluoroethanol, etc.), water, and a mixture thereof. The reaction temperature is preferably in a range of, e.g., 10° C. to 50° C., more preferably, in a range of 20° C. to 40° C., and most preferably, in a range of 25° C. to 35° C.

The reaction time may vary depending upon kind of the base used and reaction temperature, and is appropriately in a range of 0.1 minute to 24 hours in general, and preferably in a range of 1 minute to 5 hours.

In Compound (II), the compound of general formula (IIa) below (hereinafter Compound (IIa)), wherein n is 1 and L is a group (IV), can be produced by the following procedure.

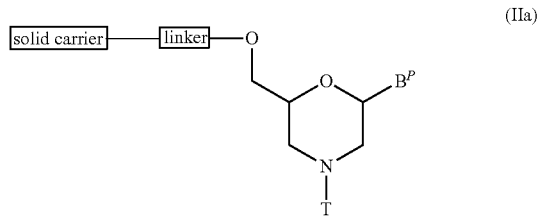

(IIa)

wherein $B^P$, T, linker and solid carrier have the same significance as defined above.

Step 1:

The compound represented by general formula (V) below is reacted with an acylating agent to prepare the compound represented by general formula (VI) below (hereinafter referred to as Compound (VI)).

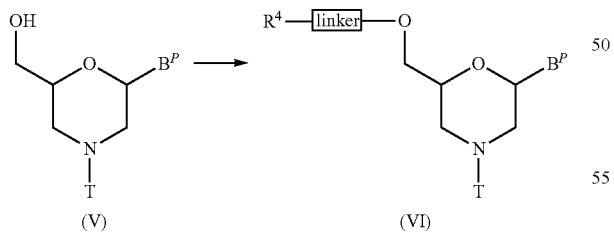

(V)          (VI)

wherein $B^P$, T and linker have the same significance as defined above; and, $R^4$ represents hydroxy, a halogen, carboxyl group or amino.

This step can be carried out by known procedures for introducing linkers, using Compound (V) as the starting material.

In particular, the compound represented by general formula (VIa) below can be produced by performing the method known as esterification, using Compound (V) and succinic anhydride.

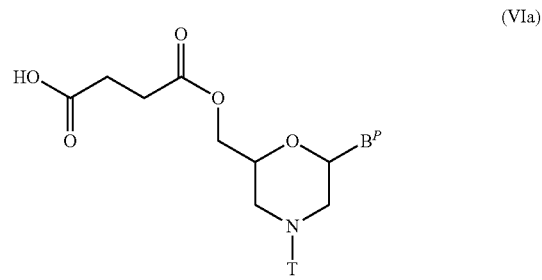

(VIa)

wherein $B^P$ and T have the same significance as defined above.

Step 2: Compound (VI) is reacted with a solid career by a condensing agent to prepare Compound (IIa).

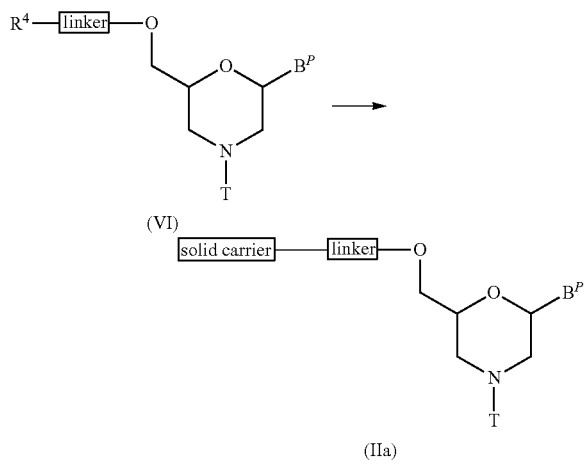

(IIa)

wherein $B^P$, $R^4$, T, linker and solid carrier have the same significance as defined above.

This step can be performed using Compound (VI) and a solid carrier in accordance with a process known as condensation reaction.

In Compound (II), the compound represented by general formula (IIa2) below wherein n is 2 to 99 (preferably a given integer of 25 to 35, 28 to 32, or 29 to 31, preferably 30) and L is a group represented by general formula (IV) can be produced by using Compound (IIa) as the starting material and repeating step A and step B of the PMO production method described in the specification for a desired number of times.

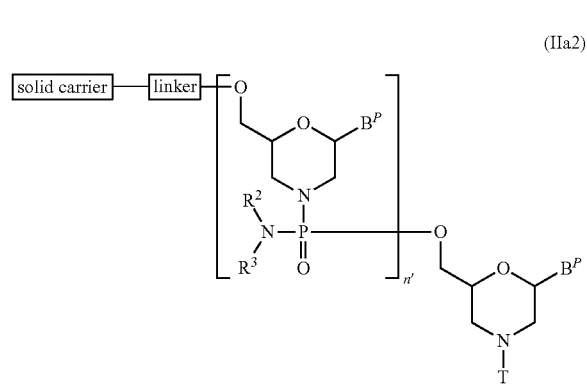

(IIa2)

wherein $B^P$, $R^2$, $R^3$, T, linker and solid carrier have the same significance as defined above; and, n' represents 1 to 98 (in a specific embodiment, n' is 1 to 34, 1 to 33, 1 to 32, 1 to 31, 1 to 30, 1 to 29, 1 to 28, 1 to 27, 1 to 26, 1 to 25, 1 to 24).

(2) Step B

Compound (III) is reacted with a morpholino monomer compound in the presence of a base to prepare the compound represented by general formula (VII) below (hereinafter referred to as Compound (VII)):

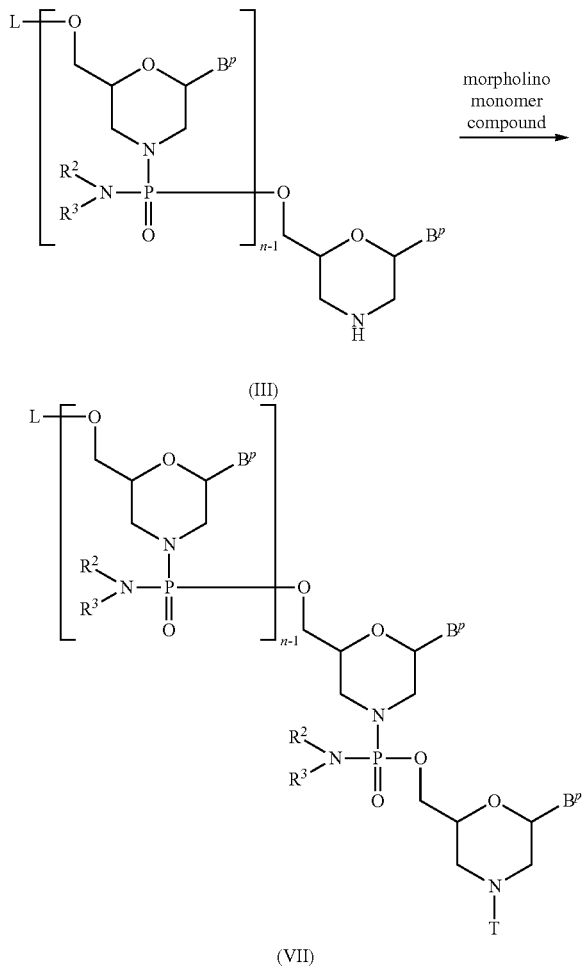

wherein $B^P$, L, n, $R^2$, $R^8$ and T have the same significance as defined above.

This step can be performed by reacting Compound (III) with the morpholino monomer compound in the presence of a base.

The morpholino monomer compound includes, for example, compounds represented by general formula (VIII) below:

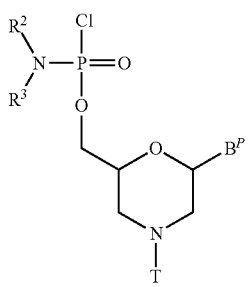

wherein $B^P$, $R^2$, $R^8$ and T have the same significance as defined above.

The "base" which can be used in this step includes, for example, diisopropylamine, triethylamine and N-ethylmorpholine. The amount of the base used is appropriately in a range of 1 mol equivalent to 1000 mol equivalents based on 1 mol of Compound (III), preferably, 10 mol equivalents to 100 mol equivalents based on 1 mol of Compound (III).

The morpholino monomer compound and base which can be used in this step may also be used as a dilution with an appropriate solvent in a concentration of 0.1% to 30%. The solvent is not particularly limited as far as it is inert to the reaction, and includes, for example, N,N-dimethylimidazolidone, N-methylpiperidone, DMF, dichloromethane, acetonitrile, tetrahydrofuran, or a mixture thereof.

The reaction temperature is preferably in a range of, e.g., 0° C. to 100° C., and more preferably, in a range of 10° C. to 50° C.

The reaction time may vary depending upon kind of the base used and reaction temperature, and is appropriately in a range of 1 minute to 48 hours in general, and preferably in a range of 30 minutes to 24 hours.

Furthermore, after completion of this step, an acylating agent can be added, if necessary. The "acylating agent" includes, for example, acetic anhydride, acetyl chloride and phenoxyacetic anhydride. The acylating agent may also be used as a dilution with an appropriate solvent in a concentration of 0.1% to 30%. The solvent is not particularly limited as far as it is inert to the reaction, and includes, for example, dichloromethane, acetonitrile, tetrahydrofuran an alcohol(s) (ethanol, isopropanol, trifluoroethanol, etc.), water, or a mixture thereof.

If necessary, a base such as pyridine, lutidine, collidine, triethylamine, diisopropylethylamine, N-ethylmorpholine, etc. may also be used in combination with the acylating agent. The amount of the acylating agent is appropriately in a range of 0.1 mol equivalent to 10000 mol equivalents, and preferably in a range of 1 mol equivalent to 1000 mol equivalents. The amount of the base is appropriately in a range of, e.g., 0.1 mol equivalent to 100 mol equivalents, and preferably in a range of 1 mol equivalent to 10 mol equivalents, based on 1 mol of the acylating agent.

The reaction temperature in this reaction is preferably in a range of 10° C. to 50° C., more preferably, in a range of 10° C. to 50° C., much more preferably, in a range of 20° C. to 4000° C., and most preferably, in a range of 25° C. to 35° C. The reaction time may vary depending upon kind of the acylating agent used and reaction temperature, and is appropriately in a range of 0.1 minute to 24 hours in general, and preferably in a range of 1 minute to 5 hours.

(3) Step C:

In Compound (VII) produced in Step B, the protective group is removed using a deprotecting agent to prepare the compound represented by general formula (IX).

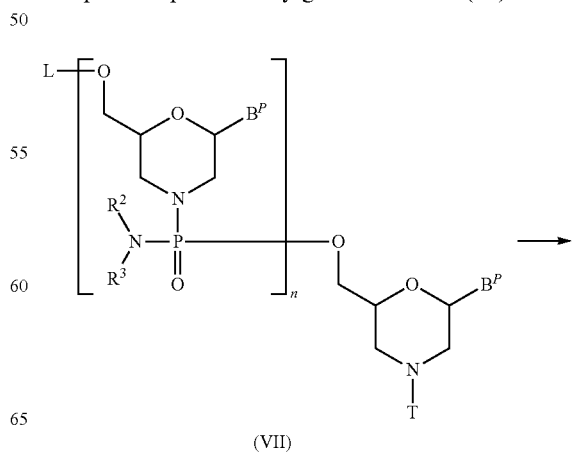

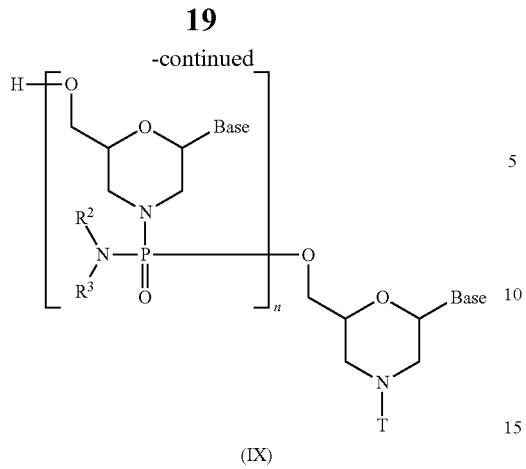

(IX)

wherein Base, $B^P$, L, n, $R^2$, $R^8$ and T have the same significance as defined above.

This step can be performed by reacting Compound (VII) with a deprotecting agent.

The "deprotecting agent" includes, e.g., conc. ammonia water and methylamine. The "deprotecting agent" used in this step may also be used as a dilution with, e.g., water, methanol, ethanol, isopropyl alcohol, acetonitrile, tetrahydrofuran, DMF N,N-dimethylimidazolidone, N-methylpiperidone, or a mixture of these solvents. Among them, ethanol is preferred. The amount of the deprotecting agent used is appropriately in a range of, 1 mol equivalent to 100000 mol equivalents, and preferably in a range of 10 mol equivalents to 1000 mol equivalents, based on 1 mol of Compound (VII).

The reaction temperature is appropriately in a range of 15° C. to 75° C., preferably, in a range of 40° C. to 70° C., and more preferably, in a range of 50° C. to 60° C. The reaction time for deprotection may vary depending upon kind of Compound (VII), reaction temperature, etc., and is appropriately in a range of 10 minutes to 30 hours, preferably 30 minutes to 24 hours, and more preferably in a range of 5 hours to 20 hours.

(4) Step D:

PMO (I) is produced by reacting Compound (IX) produced in step C with an acid:

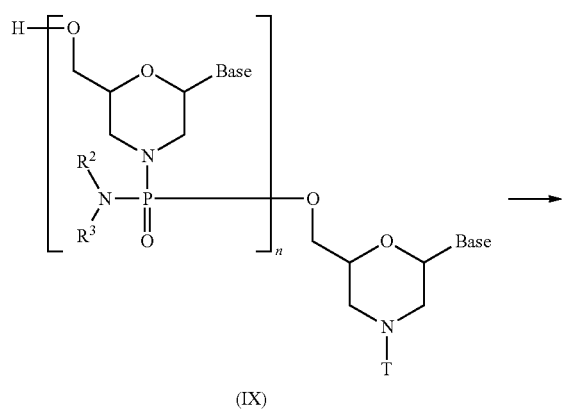

(IX)

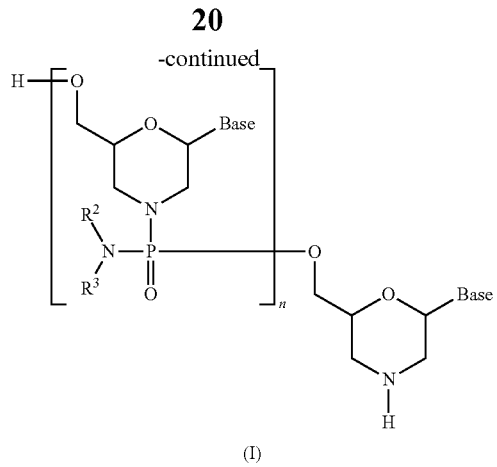

(I)

wherein Base, n, $R^2$, $R^3$ and T have the same significance as defined above.

This step can be performed by adding an acid to Compound (IX).

The "acid" which can be used in this step includes, for example, trichloroacetic acid, dichloroacetic acid, acetic acid, phosphoric acid, hydrochloric acid, etc. The acid used is appropriately used to allow the solution to have a pH range of 0.1 to 4.0, and more preferably, in a range of pH 1.0 to 3.0. The solvent is not particularly limited so long as it is inert to the reaction, and includes, for example, acetonitrile, water, or a mixture of these solvents thereof.

The reaction temperature is appropriately in a range of 10° C. to 50° C., preferably, in a range of 20° C. to 40° C., and more preferably, in a range of 25° C. to 35° C. The reaction time for deprotection may vary depending upon kind of Compound (IX), reaction temperature, etc., and is appropriately in a range of 0.1 minute to 5 hours, preferably 1 minute to 1 hour, and more preferably in a range of 1 minute to 30 minutes.

PMO (I) can be obtained by subjecting the reaction mixture obtained in this step to conventional means of separation and purification such as extraction, concentration, neutralization, filtration, centrifugal separation, recrystallization, reversed phase column chromatography $C_8$ to $C_{18}$, cation exchange column chromatography, anion exchange column chromatography, gel filtration column chromatography, high performance liquid chromatography, dialysis, ultrafiltration, etc., alone or in combination thereof. Thus, the desired PMO (I) can be isolated and purified (cf, e.g., WO 1991/09033).

In purification of PMO (I) using reversed phase chromatography, e.g., a solution mixture of 20 mM triethylamine/acetate buffer and acetonitrile can be used as an elution solvent.

In purification of PMO (I) using ion exchange chromatography, e.g., a solution mixture of 1 M saline solution and 10 mM sodium hydroxide aqueous solution can be used as an elution solvent.

A peptide nucleic acid is the oligomer of the present invention having a group represented by the following general formula as the constituent unit:

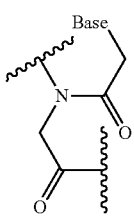

wherein Base has the same significance as defined above.

Peptide nucleic acids can be prepared by referring to, e.g., the following literatures.
1) P. E. Nielsen, M. Egholm, R. H. Berg, O. Buchardt, Science, 254, 1497 (1991)
2) M. Egholm, O. Buchardt, P. E. Nielsen, R. H. Berg, Jacs., 114, 1895 (1992)
3) K. L. Dueholmn, M. Egholm, C. Behrens, L. Christensen, H. F. Hansen, T. Vulpius, K. H. Petersen, R. H. Berg, P. E. Nielsen, O. Buchardt, J. Org. Chem., 59, 5767 (1994)
4) L. Christensen, R. Fitzpatrick, B. Gildea, K. H. Petersen, H. F. Hansen, T. Koch, M. Egholm, O. Buchardt, P. E. Nielsen, J. Coull, R. H. Berg, J. Pept. Sci., 1, 175 (1995)
5) T. Koch, H. F. Hansen, P. Andersen, T. Larsen, H. G. Batz, K. Otteson, H. Orum, J. Pept. Res., 49, 80 (1997)

In the oligomer of the present invention, the 5' end may be any of chemical structures (1) to (3) below, and preferably is (3)-OH.

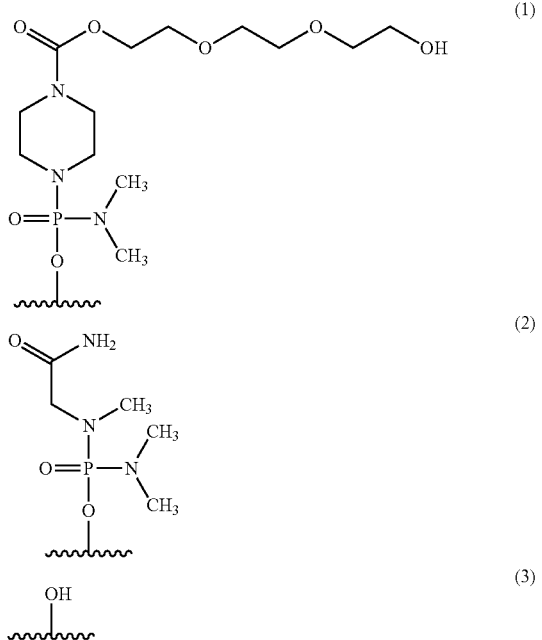

Hereinafter, the groups shown by (1), (2) and (3) above are referred to as "Group (1)," "Group (2)" and "Group (3)," respectively.

2. Pharmaceutical Composition

The oligomer of the present invention causes exon 51 skipping with a higher efficiency as compared to the prior art antisense oligomers. It is thus expected that conditions of muscular dystrophy can be relieved with high efficiency by administering the pharmaceutical composition comprising the oligomer of the present invention to DMD patients, who has mutation converting to in-frame by Exon 51 skipping, for example, patients with deletion of exon 29-50, patients with deletion of exon 50, patients with deletion of exon 45-50, patients with deletion of exon 48-50, patients with deletion of exon 49-50, patients with deletion of exon 52, patients with deletion of exon 52-63, patients with deletion of exon 13-50, patients with deletion of exon 19-50, patients with deletion of exon 43-50, or patients with deletion of exon 47-50. For example, when the pharmaceutical composition comprising the oligomer of the present invention is used, the same therapeutic effects can be achieved even in a smaller dose than that of the oligomers of the prior art. Accordingly, side effects can be alleviated and such is economical.

In another embodiment, the present invention provides the pharmaceutical composition for the treatment of muscular dystrophy, comprising as an active ingredient the oligomer of the present invention, a pharmaceutically acceptable salt or hydrate thereof (hereinafter referred to as "the composition of the present invention").

Also, the present invention provides a method for treatment of muscular dystrophy, which comprises administering to a patient of DMD the oligomer of the present invention. In the said method for treatment, the oligomer of the present invention can be administered as the pharmaceutical composition for the treatment of muscular dystrophy.

Furthermore, the present invention provides the use of the oligomer of the present invention in manufacturing of the pharmaceutical composition for treating muscular dystrophy and the oligomer of the present invention applied for the treatment of muscular dystrophy.

Examples of the pharmaceutically acceptable salt of the oligomer of the present invention contained in the composition of the present invention are alkali metal salts such as salts of sodium, potassium and lithium; alkaline earth metal salts such as salts of calcium and magnesium; metal salts such as salts of aluminum, iron, zinc, copper, nickel, cobalt, etc.; ammonium salts; organic amine salts such as salts of t-octylamine, dibenzylamine, morpholine, glucosamine, phenylglycine alkyl ester, ethylenediamine, N-methylglucamine, guanidine, diethylamine, triethylamine, dicyclohexylamine, N,N'-dibenzylethylenediamine, chloroprocaine, procaine, diethanolamine, N-benzylphenethylamine, piperazine, tetramethylammonium, tris(hydroxymethyl)aminomethane; hydrohalide salts such as salts of hydrofluorates, hydrochlorides, hydrobromides and hydroiodides; inorganic acid salts such as nitrates, perchlorates, sulfates, phosphates, etc.; lower alkane sulfonates such as methanesulfonates, trifluoromethanesulfonates and ethanesulfonates; arylsulfonates such as benzenesulfonates and p-toluenesulfonates; organic acid salts such as acetates, malates, fumarates, succinates, citrates, tartarates, oxalates, maleates, etc.; and, amino acid salts such as salts of glycine, lysine, arginine, ornithine, glutamic acid and aspartic acid. These salts may be produced by known methods. Alternatively, the oligomer of the present invention contained in the composition of the present invention may be in the form of a hydrate thereof.

Administration route for the composition of the present invention is not particularly limited so long as it is pharmaceutically acceptable route for administration, and can be chosen depending upon method of treatment. In view of easiness in delivery to muscle tissues, preferred are intravenous administration, intraarterial administration, intramuscular administration, subcutaneous administration, oral administration, tissue administration, transdermal administration, etc. Also, dosage forms which are available for the composition of the present invention are not particularly limited, and include, for example, various injections, oral agents, drips, inhalations, ointments, lotions, etc.

In administration of the oligomer of the present invention to patients with muscular dystrophy, the composition of the present invention may contain a carrier to promote delivery of the oligomer to muscle tissues. Such a carrier is not particularly limited as far as it is pharmaceutically acceptable, and examples include cationic carriers such as cationic liposomes, cationic polymers, etc., or carriers using viral envelope. The cationic liposomes are, for example, liposomes composed of 2-O-(2-diethylaminoethyl)carbamoyl-1,3-O-dioleoylglycerol and phospholipids as the essential constituents (hereinafter referred to as "liposome A"), Oligofectamine (registered trademark) (manufactured by Invitrogen Corp.), Lipofectin (registered trademark) (manufactured by Invitrogen Corp.), Lipofectamine (registered trademark) (manufactured by Invitrogen Corp.), Lipofectamine 2000 (registered trademark) (manufactured by Invitrogen Corp.), DMRIE-C(registered trademark) (manufactured by Invitrogen Corp.), GeneSilencer (registered trademark) (manufactured by Gene Therapy Systems), TransMessenger (registered trademark) (manufactured by QIAGEN, Inc.), TransIT TKO (registered trademark) (manufactured by Mirus) and Nucleofector II (Lonza). Among others, liposome A is preferred. Examples of cationic polymers are JetSI (registered trademark) (manufactured by Qbiogene, Inc.) and Jet-PEI (registered trademark) (polyethylenimine, manufactured by Qbiogene, Inc.). An example of carriers using viral envelop is GenomeOne (registered trademark) (HVJ-E liposome, manufactured by Ishihara Sangyo). Alternatively, the medical devices described in Japanese Patent No. 2924179 and the cationic carriers described in Japanese Domestic Re-Publication PCT Nos. 2006/129594 and 2008/096690 may be used as well. For further details, U.S. Pat. No. 4,235,871, U.S. Pat. No. 4,737,323, WO96/14057, "New RRC, Liposomes: A practical approach, IRL Press, Oxford (1990) pages 33-104", etc. can be referred, A concentration of the oligomer of the present invention contained in the composition of the present invention may vary depending on kind of the carrier, etc., and is appropriately in a range of 0.1 nM to 100 µM, preferably in a range of 100 nM to 10 µM. A weight ratio of the oligomer of the present invention contained in the composition of the present invention and the carrier (carrier/antisense oligomer of the present invention) may vary depending on property of the oligomer, type of the carrier, etc., and is appropriately in a range of 0.1 to 100, preferably in a range of 0.1 to 10.

In addition to the oligomer of the present invention and the carrier described above, pharmaceutically acceptable additives may also be optionally formulated in the composition of the present invention. Examples of such additives are emulsification aids (e.g., fatty acids having 6 to 22 carbon atoms and their pharmaceutically acceptable salts, albumin and dextran), stabilizers (e.g., cholesterol and phosphatidic acid), isotonizing agents (e.g., sodium chloride, glucose, maltose, lactose, sucrose, trehalose), and pH controlling agents (e.g., hydrochloric acid, sulfuric acid, phosphoric acid, acetic acid, sodium hydroxide, potassium hydroxide and triethanolamine). One or more of these additives can be used. The content of the additive in the composition of the present invention is appropriately 90 wt % or less, preferably 70 wt % or less and more preferably, 50 wt % or less.

The composition of the present invention can be prepared by adding the oligomer of the present invention to a carrier dispersion and adequately stirring the mixture. Additives may be added at an appropriate step either before or after addition of the oligomer of the present invention. An aqueous solvent that can be used in adding the oligomer of the present invention is not particularly limited as far as it is pharmaceutically acceptable, and examples are injectable water or injectable distilled water, electrolyte fluid such as physiological saline, etc., and sugar fluid such as glucose fluid, maltose fluid, etc. A person skilled in the art can appropriately choose conditions for pH and temperature for such matter.

The composition of the present invention may be prepared into, e.g., a liquid form and its lyophilized preparation. The lyophilized preparation can be prepared by lyophilizing the composition of the present invention in a liquid form in a conventional manner. The lyophilization can be performed, for example, by appropriately sterilizing the composition of the present invention in a liquid form, dispensing an aliquot into a vial container, performing preliminary freezing for 2 hours at conditions of about −40 to −20° C., performing a primary drying at about 0 to 10° C. under reduced pressure, and then performing a secondary drying at about 15 to 25° C. under reduced pressure. In general, the lyophilized preparation of the composition of the present invention can be obtained by replacing the content of the vial with nitrogen gas and capping.

The lyophilized preparation of the composition of the present invention can be used in general upon reconstitution by adding an optional suitable solution (reconstitution liquid) and redissolving the preparation. Such a reconstitution liquid includes injectable water, physiological saline and other infusion fluids. A volume of the reconstitution liquid may vary depending on the intended use, etc., is not particularly limited, and is suitably 0.5 to 2-fold greater than the volume prior to lyophilization or no more than 500 mL.

It is desired to control a dose of the composition of the present invention to be administered, by taking the following factors into account: the type and dosage form of the oligomer of the present invention contained; patients' conditions including age, body weight, etc.; administration route; and the characteristics and extent of the disease. A daily dose calculated as the amount of the antisense oligomer of the present invention is generally in a range of 0.1 mg to 10 g/human, and preferably 1 mg to 1 g/human. This numerical range may vary occasionally depending on type of the target disease, administration route and target molecule. Therefore, a dose lower than the range may be sufficient in some occasion and conversely, a dose higher than the range may be required occasionally. The composition can be administered from once to several times daily or at intervals from one day to several days.

In still another embodiment of the composition of the present invention, there is provided a pharmaceutical composition comprising a vector capable of expressing the oligonucleotide of the present invention and the carrier described above. Such an expression vector may be a vector capable of expressing a plurality of the oligonucleotides of the present invention. The composition may be formulated with pharmaceutically acceptable additives as in the case with the composition of the present invention containing the oligomer of the present invention. A concentration of the expression vector contained in the composition may vary depending upon type of the career, etc., and is appropriately in a range of 0.1 nM to 100 µM, preferably in a range of 100 nM to 10 µM. A weight ratio of the expression vector contained in the composition and the carrier (carrier/expression vector) may vary depending on property of the expression vector, type of the carrier, etc., and is appropriately in a range of 0.1 to 100, preferably in a range of 0.1 to 10. The content of the carrier contained in the composition is the same as in the case with the composition of the present invention containing the oligomer of the present invention, and a method for producing the same is also the same as in the case with the composition of the present invention.

Hereinafter, the present invention will be described in more detail with reference to EXAMPLES and TEST EXAMPLES below, but is not deemed to be limited thereto.

EXAMPLES

Reference Example 1

4-{[(2S,6R)-6-(4-Benzamido-2-oxopyrimidin-1-yl)-4-tritylmorpholin-2-yl]methoxy}-4-oxobutanoic acid Loaded onto Amino Polstyrene Resin

Step 1: Production of 4-{[(2S,6R)-6-(4-benzamido-2-oxopyrimidin-1(2H)-yl)-4-tritylmorpholin-2-yl]methoxy}-4-oxobutanoic acid Under argon atmosphere, 3.44 g of N-{1-[(2R,6S)-6-(hydroxymethyl)-4-tritylmorpholin-2-yl]-2-oxo-1,2-dihydropyrimidin-4-yl}benzamide and 1.1 g of 4-dimethylaminopyridine (4-DMAP) were suspended in 50 mL of dichloromethane, and 0.90 g of succinic anhydride was added to the suspension, followed by stirring at room temperature for 3 hours. To the reaction mixture was added 10 mL of methanol, and the mixture was concentrated under reduced pressure. The residue was extracted using ethyl acetate and 0.5 M aqueous potassium dihydrogenphosphate solution. The resulting organic layer was washed sequentially with 0.5M aqueous potassium dihydrogenphosphate solution, water and brine in the order mentioned. The resulting organic layer was dried over sodium sulfate and concentrated under reduced pressure to give 4.0 g of the product.

Step 2; Production of 4-{[(2S,6R)-6-(4-benzamido-2-oxopyrimidin-1-yl)-4-tritylmorpholin-2-yl]methoxy}-4-oxobutanoic acid Loaded onto Amino Polystyrene Resin After 4.0 g of 4-{[(2S,6R)-6-(4-benzamido-2-oxopyrimidin-1(2H)-yl)-4-tritylmorpholin-2-yl]methoxy}-4-oxobutanoic acid was dissolved in 200 mL of pyridine (dehydrated), 0.73 g of 4-DMAP and 11.5 g of 1-ethyl-3-(3-dimethylaminopropyl)carbodiimide hydrochloride were added to the solution. Then, 25.0 g of amino polystyrene resin Primer support 200 amino (manufactured GE Healthcare Japan Co., Ltd., 17-5214-97) and 8.5 mL of triethylamine were added to the mixture, followed by shaking at room temperature for 4 days. After completion of the reaction, the resin was taken out by filtration. The resulting resin was washed sequentially with pyridine, methanol and dichloromethane in the order mentioned, and dried under reduced pressure. To the resulting resin were added 200 mL of tetrahydrofuran (dehydrate), 15 mL of acetic anhydride and 15 mL of 2,6-lutidine, and the mixture was shaken at room temperature for 2 hours. The resin was taken out by filtration, washed sequentially with pyridine, methanol and dichloromethane in the order mentioned and dried under reduced pressure to give 26.7 g of the product.

The loading amount of the product was determined from the molar amount of the trityl per g resin by measuring UV absorbance at 409 nm using a known method. The loading amount of the resin was 192.2 µmol/g.

Conditions of UV Measurement
  Apparatus: U-2910 (Hitachi, Ltd.)
  Solvent: methanesulfonic acid
  Wavelength: 265 nm
  ε value: 45000

According to the descriptions in EXAMPLES 1, 2 and REFERENCE EXAMPLE 1 below, PMO shown by PMO Nos. 1-3 in TABLE 1 were synthesized. The synthesized PMO was dissolved in water for injection (manufactured by Otsuka Pharmaceutical Factory, Inc.).

TABLE 1

| PMO No. | Note | SEQ ID NO: |
|---|---|---|
| 1 | 5' end: group (3) | 1 |
| 2 | 5' end: group (3) | 2 |
| 3 | Sequence corresponding to SEQ ID NO; 588 in Patent Document 3, 5' end: group (3) | 4 |

Example 1

PMO No. 1

0.2 g 4-{[(2S,6R)-6-(4-benzamide-2-oxopyrimidin-1(2H)-yl)-4-tritylmorpholin-2-yl]methoxy}4-oxobutanoic acid supported on an aminopolystyrene resin (Reference Example 1) (26 µmol) was filled in a column with a filter tip. Then, the synthetic cycle shown below was started using an nucleic acid synthesizing machine (AKTA Oligopilot 10 plus). The desired morpholino monomer compound was added in each coupling cycle to give the nucleotide sequence of the title compound (see the Table 2 below).

TABLE 2

| Step | Reagent | Volume (mL) | Time (min) |
|---|---|---|---|
| 1 | deblocking solution | 18-32 | 1.8-3.2 |
| 2 | neutralizing and washing solution | 30 | 1.5 |
| 3 | coupling solution B | 5 | 0.5 |
| 4 | coupling solution A | 1.3 | 0.25 |
| 5 | coupling reaction by the reagents added in the steps 3 and 4 | | 120-300 |
| 6 | acetonitrile | 20 | 1.0 |
| 7 | capping solution | 9 | 2.0 |
| 8 | acetonitrile | 30 | 2.0 |

The deblocking solution used was dichloromethane solution containing 3% (w/v) trifluoroacetic acid. The neutralizing and washing solution used was a solution obtained by dissolving N,N-diisopropylethylamine to be 10% (v/v) and tetrahydrofuran to be 5% (v/v) in dichloromethane containing 35% (v/v) acetonitrile. The coupling solution A used was a solution obtained by dissolving the morpholino monomer compound in tetrahydrofuran to be 0.10 M. The coupling solution B used was a solution obtained by dissolving N,N-diisopropylethylamine to be 20% (v/v) and tetrahydrofuran to be 10% (v/v) in acetonitrile. The capping solution used was a solution obtained by dissolving 20% (v/v) acetic anhydride and 30% (v/v) 2,6-lutidine in acetonitrile.

The aminopolystyrene resin loaded with the PMO synthesized above was recovered from the reaction vessel and dried at room temperature for at least 2 hours under reduced pressure. The dried PMO loaded onto aminopolystyrene resin was charged in a reaction vessel, and 5 mL of 28% ammonia water-ethanol (1/4) was added thereto. The mixture was stirred at 55° C. for 15 hours. The aminopolystyrene resin was separated by filtration and washed with 1 mL of water-ethanol (1/4). The resulting filtrate was concentrated under reduced pressure. The resulting residue was dissolved in 10 mL of a solvent mixture of 20 mM of acetic acid—triethylamine buffer (TEAA buffer) and 10 ml of acetonitrile (4/1) and filtered through a membrane filter. The filtrate obtained was purified by reversed phase HPLC. The conditions used are as shown in Table 3 below.

TABLE 3

| Column | XBridge 5 μm C18 (Waters, φ19 × 50 mm, 1 CV = 14 mL) |
|---|---|
| Flow rate | 10 mL/min |
| Column temperature | room temperature |
| Solution A | 20 mM TEAA buffer |
| Solution B | $CH_3CN$ |
| Gradient | (B) conc. 10→70%/15 CV |

CV: column volume

Each fraction was analyzed, and the objective product was recovered and concentrated under reduced pressure. To the concentrated residue was added 0.5 mL of 2 M phosphoric acid aqueous solution, and the mixture was stirred for 15 minutes. Furthermore, 2 mL of 2 M sodium hydroxide aqueous solution was added to make the mixture alkaline, followed by filtration through a membrane filter (0.45 μm).

The resulting aqueous solution containing the objective product was purified by an anionic exchange resin column. The conditions used are as shown in Table 4 below.

TABLE 4

| Column | Source 15Q (GE Healthcare, φ10 × 108 mm, 1 CV = 8.5 mL) |
|---|---|
| Flow rate | 8.5 mL/min |
| Column temperature | room temperature |
| Solution A | 10 mM sodium hydroxide aqueous solution |
| Solution B | 10 mM sodium hydroxide aqueous solution, 1M sodium chloride aqueous solution |
| Gradient | (B) conc. 1→50%/40 CV |

Each fraction was analyzed (on HPLC) and the objective product was obtained as an aqueous solution. To the resulting aqueous solution was added 0.1 M phosphate buffer (pH 6.0) for neutralization. Next, the mixture obtained was demineralized by reversed phase HPLC under the conditions described in Table 5 below.

TABLE 5

| Column | XBridge 5 μm C8 (Waters, φ10 × 50 mm, 1 CV = 4 mL) |
|---|---|
| Flow rate | 4 mL/min |
| Column temperature | 60° C. |
| Solution A | water |
| Solution B | $CH_3CN$ |
| Gradient | (B) conc. 0→50%/20 CV |

The objective product was recovered and the mixture was concentrated under reduced pressure. The resulting residue was dissolved in water. The aqueous solution obtained was freeze-dried to give the objective compound as a white cotton-like solid.

ESI-TOF-MS Clcd.: 10021.46
Found: 10021.91

Example 2

PMO No. 2
The title compound was produced in accordance with the procedure of EXAMPLE 1.
ESI-TOF-MS Clcd.: 9916.71
Found: 9916.43

Comparative Example 1

PMO No. 3
The title compound was produced in accordance with the procedure of EXAMPLE 1.
ESI-TOF-MS Clcd.: 9949.46
Found: 9949.41

Test Example 1

In Vitro Assay
Experiments were performed using the antisense oligomers PMO Nos. 1 and 2 of the present invention and the antisense oligomer PMO No. 3. The sequences of various antisense oligomers are given in Table 6 below.

TABLE 6

| Nucleotide sequence | PMO No. | SEQ ID NO: |
|---|---|---|
| CGGTAAGTPCTGTCCTCAAGGAAGATGGCA | 1 | 1 |
| CTCATACCTTCTGCTTCAAGGAAGATGGCA | 2 | 2 |
| CTCCAACATCAAGGAAGATGCATTTCTAG | 3 | 4 |

Using an Amaxa Cell Line Nucleofector Kit L on Nucleofector II (Lonza), 0.3, 1, 3, 10 μM of the oligomers PMO Nos. 1 and 2 of the present invention and the antisense oligomer PMO No. 3 were transfected with $3.5 \times 10^5$ of RD cells (human rhabdomyosarcoma cell line). The Program T-030 was used.

After transfection, the cells were cultured for three days in 2 mL of Eagle's minimal essential medium (EMEM) (manufactured by Sigma, hereinafter the same) containing 10% fetal calf serum (FCS) (manufactured by Invitrogen) under conditions of 37° C. and 5% $CO_2$. The cells were washed with PBS (manufactured by Nissui, hereinafter the same) and 500 μl of ISOGEN II (manufactured by Nippon Gene) was added to the cells. After the cells were allowed to stand at room temperature for a few minutes to lyse the cells, the lysate was collected in an Eppendorf tube. The total RNA was extracted according to the protocol attached to ISOGEN. The concentration of the total RNA extracted was determined using a NanoDrop ND-1000 (manufactured by LMS).

One-Step RT-PCR was performed with 400 ng of the extracted total RNA using a Qiagen One Step RT-PCR Kit (manufactured by Qiagen). A reaction solution was prepared in accordance with the protocol attached to the kit. A PTC-100 (manufactured by MJ Research) was used as a thermal cycler. The RT-PCR program used is as follows.

50° C., 30 mins: reverse transcription reaction
95° C., 15 mins: thermal denaturation
[94° C., 30 seconds; 60° C., 30 seconds; 72° C., 60 seconds]×35 cycles: PCR amplification
72° C., 10 mins: final extension
The nucleotide sequences of the forward primer and reverse primer used for RT-PCR are given below.

Forward primer:
(SEQ ID NO: 5)
5'-CTGAGTGGAAGGCGGTAAAC-3'

Reverse primer:
(SEQ ID NO: 6)
5'-GAAGTTTCAGGGCCAAGTCA-3'

The reaction product, 1 μL of the RT-PCR above was analyzed using a Bioanalyzer (manufactured by Agilent Technologies, Inc.). The polynucleotide level "A" of the band with exon 51 skipping and the polynucleotide level "B" of the band without exon 51 skipping were measured. Based on these measurement values of "A" and "B", the skipping efficiency was determined by the following equation:

Skipping efficiency (%)=$A/(A+B)$×100

Experimental Results

The results are shown in FIG. 1. This experiment revealed that, the antisense oligomers of the present invention could cause exon 51 skipping with a markedly higher efficiency than the antisense oligomer PMO No. 3.

Example 3

PMO No. 4-6

The title compound was produced in accordance with the procedure of EXAMPLE 1. The sequences of various antisense oligomers are given below.

TABLE 7

| PMO No. | Sequence | ESI-TOF-MS MW | Found | Note | SEQ ID NO |
|---|---|---|---|---|---|
| 4 | AACATCAAGGAAGATGGCATT | 7007.96 | 7007.97 | 5' end: group (3) | 7 |
| 5 | TCCAACATCAAGGAAGATGGC | 6968.97 | 6968.42 | 5' end: group (3) | 8 |
| 6 | ACCTCCAACATCAAGGAAGAT | 6912.91 | 6912.85 | 5' end: group (3) | 9 |

Example 4

2'-O-methoxy-phosphorothioates Shown by SEQ ID NOS: 9 to 33

Various antisense oligomers of the title were produced by outsourcing to Japan Bio Service Co. The sequence of various antisense oligomers are given in Table 8.

TABLE 8

| SEQ ID NO: | Sequence | ESI-TOF-MS MW | Found |
|---|---|---|---|
| 10 | GAGUAACAGUCUGAGUAGGAG | 7453 | 7452.876 |
| 11 | UGUGUCACCAGAGUAACAGUC | 7310 | 7313.793 |
| 12 | AACCACAGGUUGUGUCACCAG | 7309 | 7311.199 |
| 13 | UUUCCUUAGUAACCACAGGUU | 7209 | 7211.436 |
| 14 | GAGAUGGCAGUUUCCUUAGUA | 7328 | 7331.388 |
| 15 | UUCUAGUUUGGAGAUGGCAGU | 7345 | 7347.440 |
| 16 | AAGAUGGCAUUUCUAGUUUGG | 7329 | 7329.982 |
| 17 | AACAUCAAGGAAGAUGGCAUU | 7381 | 7381.059 |
| 18 | AGGUACCUCCAACAUCAAGGA | 7316 | 7318.395 |
| 19 | CUGCCAGAGCAGGUACCUCCA | 7284 | 7286.932 |
| 20 | CGGUUGAAAUCUGCCAGAGCA | 7349 | 7351.895 |
| 21 | UGUCCAAGCCCGGUUGAAAUC | 7286 | 7286.00 |
| 22 | CGGUAAGUUCUGUCCAAGCCC | 7262 | 7262.929 |
| 23 | GAAAGCCAGUCGUAAGUUCU | 7350 | 7351.869 |
| 24 | AUCAAGCAGAGAAAGCCAGUC | 7379 | 7378.383 |
| 25 | UUAUAACUUGAUCAAGCAGAG | 7319 | 7320.149 |
| 26 | CUCUGUGAUUUUAUAACUUGA | 7211 | 7212.295 |
| 27 | CACCAUCACCCUCUGUGAUUU | 7144 | 7145.555 |
| 28 | CAAGGUCACCCACCAUCACCC | 7187 | 7187.709 |
| 29 | UUGAUAUCCUCAAGGUCACCC | 7207 | 7210.071 |
| 30 | GAUCAUCUCGUUGAUAUCCUC | 7185 | 71882.39 |
| 31 | UCUGCUUGAUGAUCAUCUCGU | 7202 | 7203.926 |
| 32 | GGCAUUUCUAGUUUGGAGAUG | 7346 | 7346.562 |
| 33 | CAAGGAAGAUGGCAUUUCUAG | 7375 | 7375.678 |
| 34 | CCUCCAACAUCAAGGAAGAUG | 7317 | 7318.343 |

INDUSTRIAL APPLICABILITY

Experimental results in TEST EXAMPLES demonstrate that the oligomers of the present invention caused exon 51 skipping with a markedly high efficiency in RD cells. Therefore, the oligomers of the present invention are extremely useful for the treatment of DMD.

The invention claimed is:

1. An antisense oligomer of 25-35 nucleobases, or a pharmaceutically acceptable salt or hydrate thereof, wherein the antisense oligomer is a morpholino oligomer, a peptide nucleic acid (PNA), or an oligonucleotide comprising at least one nucleotide having:

(i) a modified sugar moiety, wherein the 2'—OH group of a ribose is replaced by any one selected from the group consisting of R, R'OR, SH, SR, NH$_2$, NHR, NR$_2$, N$_3$, CN, F, CI, Br and I (wherein R is an alkyl or an aryl and R' is an alkylene), or (ii) a modified phosphate-binding region selected from the group consisting of a phosphorothioate bond, a phosphorodithioate bond, an alkylphosphonate bond, a phosphoramidate bond, and a boranophosphate bond, and wherein the antisense oligomer is:

(a) an antisense oligomer comprising the nucleobase sequence of SEQ ID NO: 1or 2; or (b) an antisense oligomer which i) consists of a nucleobase sequence that differs from the nucleobase sequence of SEQ ID NO: 1 or 2 by no more than 5nucleobases, wherein each difference independently may be a deletion, a substitution, an insertion, or an addition of a nucleobase, and ii) has an activity to cause skipping of the 51st exon of a human dystrophin gene.

2. The antisense oligomer or a pharmaceutically acceptable salt or hydrate thereof according to claim 1, wherein the antisense oligomer is:

(c) an antisense oligomer which consists of the nucleobase sequence of SEQ ID NO: 1 or 2; or (d) an antisense oligomer which consists of a nucleobase sequence that differs from the nucleobase sequence of SEQ ID NO: 1 or 2 by no more than 3 nucleobases.

3. The antisense oligomer according to claim 1, which is a morpholino oligomer, or a pharmaceutically acceptable salt or hydrate thereof.

4. The antisense oligomer according to claim 3, which is a phosphorodiamidate morpholino oligomer, or a pharmaceutically acceptable salt or hydrate thereof.

5. The antisense oligomer according to claim 3, or a pharmaceutically acceptable salt or hydrate thereof, wherein the 5' end is any one of chemical formulae (1) to (3) below:

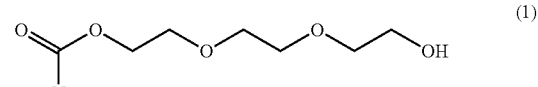

6. A pharmaceutical composition for the treatment of muscular dystrophy, comprising as an active ingredient the antisense oligomer, or a pharmaceutically acceptable salt or hydrate thereof according to claim 1.

7. The pharmaceutical composition according to claim 6, comprising a pharmaceutically acceptable carrier.

8. A method for treatment of muscular dystrophy, which comprises administering to a patient with muscular dystrophy an antisense oligomer of 25-35 nucleobases, or a pharmaceutically acceptable salt or hydrate thereof, wherein the antisense oligomer is:

(a) an antisense oligomer comprising the nucleobase sequence of SEQ ID NO: 1 or 2; or (b) an antisense oligomer which i) consists of a nucleobase sequence that differs from the nucleobase sequence of SEQ ID NO: 1 or 2 by no more than 5 nucleobases, wherein each difference independently may be a deletion, a substitution, an insertion, or an addition of a nucleobase, and ii) has an activity to cause skipping of the 51st exon of a human dystrophin gene; wherein the antisense oligomer is a morpholino oligomer, a peptide nucleic acid (PNA), or an oligonucleotide that the sugar moiety and/or the phosphate-binding region of at least one nucleotide constituting the oligonucleotide is modified, and wherein the patient with muscular dystrophy has a mutation converting to in-frame by exon 51 skipping.

9. The method for treatment according to claim 8, wherein the patient with muscular dystrophy is a patient with deletions of exons 29-50, 50, 45-50, 48-50, 49-50, 52, 52-63, 13-50, 19-50, 43-50 or 47-50.

10. The method for treatment according to claim 8, wherein the patient is a human.

* * * * *